(12) United States Patent
Hobot et al.

(10) Patent No.: US 11,642,654 B2
(45) Date of Patent: *May 9, 2023

(54) ZIRCONIUM OXIDE MODULE CONDITIONING

(71) Applicant: Medtronic, Inc., Minneapolis, MN (US)

(72) Inventors: Christopher M. Hobot, Rogers, MN (US); Bryant J. Pudil, Plymouth, MN (US)

(73) Assignee: Medtronic, Inc, Minneapolis, MN (US)

( * ) Notice: Subject to any disclaimer, the term of this patent is extended or adjusted under 35 U.S.C. 154(b) by 157 days.

This patent is subject to a terminal disclaimer.

(21) Appl. No.: 17/197,665

(22) Filed: Mar. 10, 2021

(65) Prior Publication Data
US 2021/0187481 A1 Jun. 24, 2021

Related U.S. Application Data

(63) Continuation of application No. 15/798,233, filed on Oct. 30, 2017, now Pat. No. 10,981,148.
(Continued)

(51) Int. Cl.
| | |
|---|---|
| *B01J 20/34* | (2006.01) |
| *A61M 1/16* | (2006.01) |
| *B01J 20/28* | (2006.01) |
| *B01J 49/57* | (2017.01) |
| *B01J 49/08* | (2017.01) |

(Continued)

(52) U.S. Cl.
CPC ......... *B01J 20/3475* (2013.01); *A61L 2/0088* (2013.01); *A61M 1/168* (2013.01); *A61M 1/1696* (2013.01); *B01D 15/00* (2013.01); *B01J 20/0211* (2013.01); *B01J 20/0292* (2013.01); *B01J 20/06* (2013.01); *B01J 20/28052* (2013.01); *B01J 20/3433* (2013.01); *B01J 49/07* (2017.01); *B01J 49/08* (2017.01); *B01J 49/57* (2017.01); *C01B 25/372* (2013.01); *C01G 25/02* (2013.01); *A61L 2202/17* (2013.01); *A61L 2202/24* (2013.01); *A61M 2205/3324* (2013.01); *A61M 2205/3331* (2013.01)

(58) Field of Classification Search
None
See application file for complete search history.

(56) References Cited

U.S. PATENT DOCUMENTS

| | | |
|---|---|---|
| 1,617,288 A | 2/1927 | Kenney |
| 2,703,313 A | 1/1950 | Gill |

(Continued)

FOREIGN PATENT DOCUMENTS

| | | |
|---|---|---|
| CN | 1487853 A | 4/2004 |
| CN | 102573618 | 7/2012 |

(Continued)

OTHER PUBLICATIONS

Office Action in U.S. Appl. No. 14/269,589, dated Nov. 4, 2016.
(Continued)

*Primary Examiner* — Richard C Gurtowski

(57) ABSTRACT

The invention relates to devices, systems, and methods for conditioning a zirconium oxide sorbent module for use in dialysis after recharging. The devices, systems, and methods can provide for conditioning and recharging of zirconium oxide in a single system, or in separate systems.

20 Claims, 7 Drawing Sheets

Related U.S. Application Data

(60) Provisional application No. 62/427,806, filed on Nov. 29, 2016.

(51) Int. Cl.

| | | |
|---|---|---|
| B01J 49/07 | (2017.01) | |
| A61L 2/00 | (2006.01) | |
| B01D 15/00 | (2006.01) | |
| B01J 20/02 | (2006.01) | |
| B01J 20/06 | (2006.01) | |
| C01B 25/37 | (2006.01) | |
| C01G 25/02 | (2006.01) | |

(56) References Cited

U.S. PATENT DOCUMENTS

| | | |
|---|---|---|
| 3,608,729 A | 9/1971 | Haselden |
| 3,617,545 A | 11/1971 | Dubois |
| 3,617,558 A | 11/1971 | Jones |
| 3,669,878 A | 6/1972 | Marantz |
| 3,669,880 A | 6/1972 | Marantz |
| 3,776,819 A | 12/1973 | Williams |
| 3,840,835 A | 10/1974 | Kussy |
| 3,850,835 A | 11/1974 | Marantz |
| 3,884,808 A | 5/1975 | Scott |
| 3,902,490 A | 9/1975 | Jacobsen |
| 3,989,622 A | 11/1976 | Marantz |
| 4,060,485 A | 11/1977 | Eaton |
| 4,073,725 A | 2/1978 | Takeuchi |
| 4,094,775 A | 6/1978 | Mueller |
| 4,142,845 A | 3/1979 | Lepp |
| 4,192,748 A | 3/1980 | Hyden |
| 4,206,054 A | 6/1980 | Moore |
| 4,209,392 A | 6/1980 | Wallace |
| 4,269,708 A | 5/1981 | Bonomini |
| 4,371,385 A | 2/1983 | Johnson |
| 4,374,382 A | 2/1983 | Markowitz |
| 4,376,707 A | 3/1983 | Lehmann |
| 4,381,999 A | 5/1983 | Boucher |
| 4,460,555 A | 7/1984 | Thompson |
| 4,556,063 A | 12/1985 | Thompson |
| 4,562,751 A | 1/1986 | Nason |
| 4,581,141 A | 4/1986 | Ash |
| 4,612,122 A | 9/1986 | Ambrus |
| 4,650,587 A | 3/1987 | Polak |
| 4,661,246 A | 4/1987 | Ash |
| 4,678,408 A | 7/1987 | Mason |
| 4,684,460 A | 8/1987 | Issautier |
| 4,685,903 A | 8/1987 | Cable |
| 4,687,582 A | 8/1987 | Dixon |
| 4,750,494 A | 6/1988 | King |
| 4,765,907 A | 8/1988 | Scott |
| 4,826,663 A | 5/1989 | Alberti |
| 4,828,693 A | 5/1989 | Lindsay |
| 5,032,615 A | 7/1991 | Ward et al. |
| 5,047,014 A | 9/1991 | Mosebach et al. |
| 5,080,653 A | 1/1992 | Voss |
| 5,092,886 A | 3/1992 | Dobos-Hardy |
| 5,097,122 A | 3/1992 | Coiman |
| 5,127,404 A | 7/1992 | Wyborny |
| 5,192,132 A | 3/1993 | Pelensky |
| 5,230,702 A | 7/1993 | Lindsay |
| 5,284,470 A | 2/1994 | Beltz |
| 5,302,288 A | 4/1994 | Meidl |
| 5,305,745 A | 4/1994 | Zacouto |
| 5,308,315 A | 5/1994 | Khuri |
| 5,318,750 A | 6/1994 | Lascombes |
| 5,399,157 A | 3/1995 | Goux |
| 5,441,049 A | 8/1995 | Masano |
| 5,442,969 A | 8/1995 | Troutner |
| 5,445,610 A | 8/1995 | Evert |
| 5,468,388 A | 11/1995 | Goddard |
| 5,507,723 A | 4/1996 | Keshaviah |
| 5,662,806 A | 9/1997 | Keshaviah et al. |
| 5,683,432 A | 11/1997 | Goedeke |
| 5,685,835 A * | 11/1997 | Brugger ............ A61M 1/1688 422/28 |
| 5,685,988 A | 11/1997 | Malchesky |
| 5,716,400 A | 2/1998 | Davidson |
| 5,744,031 A | 4/1998 | Bene |
| 5,762,782 A | 6/1998 | Kenley |
| 5,770,086 A | 6/1998 | Indriksons |
| 5,849,179 A | 12/1998 | Emerson |
| 5,858,186 A | 1/1999 | Glass |
| 5,938,634 A | 8/1999 | Packard |
| 5,938,938 A | 8/1999 | Bosetto |
| 5,944,684 A | 8/1999 | Roberts |
| 6,036,858 A | 3/2000 | Carlsson |
| 6,048,732 A | 4/2000 | Anslyn |
| 6,052,622 A | 4/2000 | Holmstrom |
| 6,058,331 A | 5/2000 | King |
| 6,114,176 A | 9/2000 | Edgson et al. |
| 6,126,831 A | 10/2000 | Goldau |
| 6,171,480 B1 | 1/2001 | Lee |
| 6,230,059 B1 | 5/2001 | Duffin |
| 6,248,093 B1 | 6/2001 | Moberg |
| 6,254,567 B1 | 7/2001 | Treu |
| 6,321,101 B1 | 11/2001 | Holmstrom |
| 6,362,591 B1 | 3/2002 | Moberg |
| 6,363,279 B1 | 3/2002 | Ben-Haim |
| 6,390,969 B1 | 5/2002 | Bolling et al. |
| 6,491,993 B1 | 12/2002 | Forbes |
| 6,521,184 B1 | 2/2003 | Edgson et al. |
| 6,554,798 B1 | 4/2003 | Mann |
| 6,555,986 B2 | 4/2003 | Moberg |
| 6,565,525 B1 | 5/2003 | Burbank et al. |
| 6,572,769 B2 | 6/2003 | Rajan |
| 6,579,460 B1 | 6/2003 | Willis |
| 6,585,675 B1 | 7/2003 | O'Mahony et al. |
| 6,589,229 B1 | 7/2003 | Connelly |
| 6,593,747 B2 | 7/2003 | Puskas |
| 6,596,234 B1 | 7/2003 | Schnell et al. |
| 6,602,399 B1 | 8/2003 | Fromherz |
| 6,627,164 B1 | 9/2003 | Wong |
| 6,666,840 B1 | 12/2003 | Falkvall et al. |
| 6,676,608 B1 | 1/2004 | Keren |
| 6,695,807 B2 | 2/2004 | Bell et al. |
| 6,711,439 B1 | 3/2004 | Bradley |
| 6,719,745 B1 | 4/2004 | Taylor |
| 6,773,412 B2 | 8/2004 | O'Mahony et al. |
| 6,814,724 B2 | 11/2004 | Taylor |
| 6,818,196 B2 | 11/2004 | Wong |
| 6,861,266 B1 | 3/2005 | Sternby |
| 6,878,258 B2 | 4/2005 | Hughes |
| 6,878,283 B2 | 4/2005 | Thompson |
| 6,878,285 B2 | 4/2005 | Hughes |
| 6,890,315 B1 | 5/2005 | Levin |
| 6,923,782 B2 | 8/2005 | O'Mahony et al. |
| 6,960,179 B2 | 11/2005 | Gura |
| 7,029,456 B2 | 4/2006 | Ware et al. |
| 7,033,498 B2 | 4/2006 | Wong |
| 7,077,819 B1 | 7/2006 | Goldau |
| 7,097,630 B2 | 8/2006 | Gotch |
| 7,101,519 B2 | 9/2006 | Wong |
| 7,128,750 B1 | 10/2006 | Stergiopulos |
| 7,153,693 B2 | 12/2006 | Tajiri |
| 7,208,092 B2 | 4/2007 | Micheli |
| 7,241,272 B2 | 7/2007 | Karoor |
| 7,276,042 B2 | 10/2007 | Polaschegg |
| 7,309,323 B2 | 12/2007 | Gura |
| 7,318,892 B2 | 1/2008 | Connell |
| 7,326,576 B2 | 2/2008 | Womble et al. |
| 7,384,543 B2 | 6/2008 | Jonsson et al. |
| 7,435,342 B2 | 10/2008 | Tsukamoto |
| 7,462,161 B2 | 12/2008 | O'Mahony et al. |
| 7,488,447 B2 | 2/2009 | Sternby |
| 7,537,688 B2 | 5/2009 | Tarumi |
| 7,544,300 B2 | 6/2009 | Brugger |
| 7,544,737 B2 | 6/2009 | Poss |
| 7,563,240 B2 | 7/2009 | Gross |
| 7,566,432 B2 | 7/2009 | Wong |
| 7,575,564 B2 | 8/2009 | Childers |
| 7,597,806 B2 | 10/2009 | Uchi |
| 7,674,231 B2 | 3/2010 | Mccombie |

(56) References Cited

U.S. PATENT DOCUMENTS

| | | |
|---|---|---|
| 7,674,237 B2 | 3/2010 | O'Mahony et al. |
| 7,686,778 B2 | 3/2010 | Burbank et al. |
| 7,704,361 B2 | 4/2010 | Garde |
| 7,736,507 B2 | 6/2010 | Wong |
| 7,754,852 B2 | 7/2010 | Burnett |
| 7,756,572 B1 | 7/2010 | Fard |
| 7,776,001 B2 | 8/2010 | Brugger et al. |
| 7,776,006 B2 | 8/2010 | Childers |
| 7,776,210 B2 | 8/2010 | Rosenbaum |
| 7,794,141 B2 | 9/2010 | Perry |
| 7,794,419 B2 | 9/2010 | Paolini |
| 7,850,635 B2 | 12/2010 | Polaschegg |
| 7,867,214 B2 | 1/2011 | Childers |
| 7,901,376 B2 | 3/2011 | Steck et al. |
| 7,905,853 B2 | 3/2011 | Chapman et al. |
| 7,922,686 B2 | 4/2011 | Childers |
| 7,922,911 B2 | 4/2011 | Micheli |
| 7,947,179 B2 | 5/2011 | Rosenbaum |
| 7,955,289 B2 | 6/2011 | O'Mahony et al. |
| 7,955,290 B2 | 6/2011 | Karoor |
| 7,967,022 B2 | 6/2011 | Grant |
| 7,981,082 B2 | 7/2011 | Wang |
| 7,988,854 B2 | 8/2011 | Tsukamoto |
| 8,002,726 B2 | 8/2011 | Karoor |
| 8,012,118 B2 | 9/2011 | Curtin |
| 8,029,454 B2 | 10/2011 | Kelly |
| 8,034,161 B2 | 10/2011 | Gura |
| 8,066,658 B2 | 11/2011 | Karoor |
| 8,070,709 B2 | 12/2011 | Childers |
| 8,080,161 B2 | 12/2011 | Ding et al. |
| 8,087,303 B2 | 1/2012 | Beavis |
| 8,096,969 B2 | 1/2012 | Roberts |
| 8,180,574 B2 | 5/2012 | Lo |
| 8,182,673 B2 | 5/2012 | Childers et al. |
| 8,183,046 B2 | 5/2012 | Lu |
| 8,187,250 B2 | 5/2012 | Roberts |
| 8,197,439 B2 | 6/2012 | Wang |
| 8,206,591 B2 | 6/2012 | Kotanko et al. |
| 8,211,048 B2 | 7/2012 | Szamosfalvi et al. |
| 8,221,529 B2 | 7/2012 | Childers et al. |
| 8,226,595 B2 | 7/2012 | Childers et al. |
| 8,246,826 B2 | 8/2012 | Wilt |
| 8,267,881 B2 | 9/2012 | O'Mahony et al. |
| 8,273,049 B2 | 9/2012 | Demers |
| 8,292,594 B2 | 10/2012 | Tracey |
| 8,303,532 B2 | 11/2012 | Hamada |
| 8,313,642 B2 | 11/2012 | Yu |
| 8,317,492 B2 | 11/2012 | Demers |
| 8,357,113 B2 | 1/2013 | Childers |
| 8,357,298 B2 | 1/2013 | Demers et al. |
| 8,366,316 B2 | 2/2013 | Kamen |
| 8,366,655 B2 | 2/2013 | Kamen |
| 8,376,999 B2 | 2/2013 | Busby et al. |
| 8,377,012 B2 | 2/2013 | Chapman et al. |
| 8,377,308 B2 | 2/2013 | Kreymann et al. |
| 8,388,567 B2 | 3/2013 | Rovatti |
| 8,404,491 B2 | 3/2013 | Li |
| 8,409,441 B2 | 4/2013 | Wilt |
| 8,409,444 B2 | 4/2013 | Wong |
| 8,449,487 B2 | 5/2013 | Hovland et al. |
| 8,480,607 B2 | 7/2013 | Davies |
| 8,499,780 B2 | 8/2013 | Wilt |
| 8,518,260 B2 | 8/2013 | Raimann |
| 8,535,525 B2 | 9/2013 | Heyes |
| 8,580,112 B2 | 11/2013 | Updyke |
| 8,597,227 B2 | 12/2013 | Childers |
| 8,647,506 B2 | 2/2014 | Wong |
| 8,696,626 B2 | 4/2014 | Kirsch |
| 8,733,559 B2 | 5/2014 | Wong |
| 8,764,981 B2 | 7/2014 | Ding |
| 8,777,892 B2 | 7/2014 | Sandford |
| 8,903,492 B2 | 12/2014 | Soykan |
| 9,144,640 B2 | 9/2015 | Pudil |
| 9,254,355 B2 | 2/2016 | Sandford |
| 9,527,015 B2 | 12/2016 | Chau |
| 10,695,481 B2 | 6/2020 | Kelly |
| 10,981,148 B2* | 4/2021 | Hobot ............ B01D 15/00 |
| 2001/0007931 A1 | 7/2001 | Blatter |
| 2001/0009756 A1 | 7/2001 | Hei et al. |
| 2002/0016550 A1 | 2/2002 | Sweeney |
| 2002/0027106 A1 | 3/2002 | Smith |
| 2002/0042561 A1 | 4/2002 | Schulman |
| 2002/0062098 A1 | 5/2002 | Cavicchioli et al. |
| 2002/0112609 A1 | 8/2002 | Wong |
| 2002/0117436 A1 | 8/2002 | Rajan |
| 2002/0147109 A1* | 10/2002 | Branover ............ B01J 20/3028 |
| | | 423/229 |
| 2003/0080059 A1 | 5/2003 | Peterson |
| 2003/0097086 A1 | 5/2003 | Gura |
| 2003/0105435 A1 | 6/2003 | Taylor |
| 2003/0113931 A1 | 6/2003 | Pan |
| 2003/0114787 A1 | 6/2003 | Gura |
| 2003/0138348 A1 | 7/2003 | Bell et al. |
| 2003/0187479 A1 | 10/2003 | Thong |
| 2004/0019312 A1 | 1/2004 | Childers |
| 2004/0019320 A1 | 1/2004 | Childers |
| 2004/0030277 A1 | 2/2004 | O'Mahony et al. |
| 2004/0037986 A1 | 2/2004 | Houston et al. |
| 2004/0054315 A1 | 3/2004 | Levin et al. |
| 2004/0082903 A1 | 4/2004 | Micheli |
| 2004/0084358 A1 | 5/2004 | O'Mahony et al. |
| 2004/0099593 A1 | 5/2004 | DePaolis |
| 2004/0127648 A1* | 7/2004 | Guerrier ............ C08L 33/24 |
| | | 525/227 |
| 2004/0147900 A1 | 7/2004 | Polaschegg |
| 2004/0168963 A1 | 9/2004 | King |
| 2004/0215090 A1 | 10/2004 | Erkkila |
| 2004/0257409 A1 | 12/2004 | Cheok |
| 2005/0006296 A1 | 1/2005 | Sullivan |
| 2005/0056592 A1 | 3/2005 | Braunger |
| 2005/0065760 A1 | 3/2005 | Murtfeldt |
| 2005/0101901 A1 | 5/2005 | Gura |
| 2005/0113796 A1 | 5/2005 | Taylor |
| 2005/0126961 A1 | 6/2005 | Bissler |
| 2005/0131332 A1 | 6/2005 | Kelly |
| 2005/0126998 A1 | 7/2005 | Childers |
| 2005/0148923 A1 | 7/2005 | Sternby |
| 2005/0150832 A1 | 7/2005 | Tsukamoto |
| 2005/0230313 A1 | 10/2005 | O'Mahony et al. |
| 2005/0234354 A1 | 10/2005 | Rowlandson |
| 2005/0234381 A1 | 10/2005 | Niemetz |
| 2005/0274658 A1 | 12/2005 | Rosenbaum |
| 2006/0025661 A1 | 2/2006 | Sweeney |
| 2006/0037483 A1 | 2/2006 | Kief |
| 2006/0217771 A1 | 2/2006 | Soykan |
| 2006/0157413 A1 | 7/2006 | Bene |
| 2006/0189926 A1 | 8/2006 | Hall et al. |
| 2006/0195064 A1 | 8/2006 | Plahey |
| 2006/0226079 A1 | 10/2006 | Mori |
| 2006/0241543 A1 | 10/2006 | Gura |
| 2006/0241709 A1 | 10/2006 | Soykan |
| 2006/0264894 A1 | 11/2006 | Moberg |
| 2007/0007208 A1 | 1/2007 | Brugger |
| 2007/0055296 A1 | 3/2007 | Stergiopulos |
| 2007/0066928 A1 | 3/2007 | Lannoy |
| 2007/0138011 A1 | 6/2007 | Hofmann |
| 2007/0175827 A1 | 8/2007 | Wariar |
| 2007/0179431 A1 | 8/2007 | Roberts |
| 2007/0213665 A1 | 9/2007 | Curtin |
| 2007/0215545 A1 | 9/2007 | Bissler |
| 2007/0243113 A1 | 10/2007 | DiLeo |
| 2007/0255250 A1 | 11/2007 | Moberg |
| 2008/0006570 A1 | 1/2008 | Gura |
| 2008/0011664 A1 | 1/2008 | Karoor |
| 2008/0015493 A1 | 1/2008 | Childers et al. |
| 2008/0021337 A1 | 1/2008 | Li |
| 2008/0051696 A1 | 2/2008 | Curtin |
| 2008/0053905 A9 | 3/2008 | Brugger |
| 2008/0067132 A1 | 3/2008 | Ross |
| 2008/0215247 A1 | 9/2008 | Tonelli |
| 2008/0217245 A1 | 9/2008 | Rambod |
| 2008/0241031 A1 | 10/2008 | Li |
| 2008/0292935 A1 | 11/2008 | Roelofs |
| 2009/0012864 A1 | 1/2009 | Goldberg |

(56) References Cited

U.S. PATENT DOCUMENTS

| | | |
|---|---|---|
| 2009/0020471 A1 | 1/2009 | Tsukamoto |
| 2009/0078636 A1 | 3/2009 | Uchi |
| 2009/0084199 A1 | 4/2009 | Wright |
| 2009/0101552 A1 | 4/2009 | Fulkerson |
| 2009/0101577 A1 | 4/2009 | Fulkerson |
| 2009/0120864 A1 | 5/2009 | Fulkerson |
| 2009/0127193 A1 | 5/2009 | Updyke |
| 2009/0149795 A1 | 6/2009 | O'Mahony et al. |
| 2009/0216045 A1 | 8/2009 | Singh |
| 2009/0266358 A1 | 10/2009 | Sacristan Rock |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2010/0004588 A1 | 1/2010 | Yeh |
| 2010/0007838 A1 | 1/2010 | Fujimoto |
| 2010/0010429 A1 | 1/2010 | Childers |
| 2010/0018923 A1 | 1/2010 | Rohde et al. |
| 2010/0030151 A1 | 2/2010 | Kirsch |
| 2010/0051529 A1 | 3/2010 | Grant et al. |
| 2010/0051552 A1 | 3/2010 | Rohde |
| 2010/0076364 A1 | 3/2010 | O'Mahony et al. |
| 2010/0078381 A1 | 4/2010 | Merchant |
| 2010/0078387 A1 | 4/2010 | Wong |
| 2010/0084330 A1 | 4/2010 | Wong |
| 2010/0094158 A1 | 4/2010 | Solem et al. |
| 2010/0100027 A1 | 4/2010 | Schilthuizen et al. |
| 2010/0101195 A1 | 4/2010 | Clements et al. |
| 2010/0102190 A1 | 4/2010 | Zhu et al. |
| 2010/0114001 A1 | 5/2010 | O'Mahony |
| 2010/0114012 A1 | 5/2010 | Sandford et al. |
| 2010/0137693 A1 | 6/2010 | Porras et al. |
| 2010/0168546 A1 | 7/2010 | Kamath et al. |
| 2010/0168641 A1 | 7/2010 | O'Mahony et al. |
| 2010/0213127 A1 | 8/2010 | Castellarnau |
| 2010/0217181 A1 | 8/2010 | Roberts |
| 2010/0224492 A1 | 9/2010 | Ding et al. |
| 2010/0234795 A1 | 9/2010 | Wallenas |
| 2010/0241045 A1 | 9/2010 | Kelly |
| 2010/0252490 A1 | 10/2010 | Fulkerson |
| 2010/0312172 A1 | 12/2010 | Hoffman |
| 2010/0312174 A1 | 12/2010 | Hoffman |
| 2010/0314314 A1 | 12/2010 | Ding |
| 2010/0326911 A1 | 12/2010 | Rosenbaum |
| 2011/0009798 A1 | 1/2011 | Kelly |
| 2011/0017665 A1 | 1/2011 | Updyke |
| 2011/0048949 A1 | 3/2011 | Ding et al. |
| 2011/0066043 A1 | 3/2011 | Banet |
| 2011/0077574 A1 | 3/2011 | Sigg |
| 2011/0079558 A1 | 4/2011 | Raimann |
| 2011/0087187 A1 | 4/2011 | Beck |
| 2011/0130666 A1 | 6/2011 | Dong |
| 2011/0163034 A1 | 7/2011 | Castellarnau |
| 2011/0171713 A1 | 7/2011 | Bluchel |
| 2011/0184340 A1 | 7/2011 | Tan |
| 2011/0220562 A1 | 9/2011 | Beiriger |
| 2011/0247973 A1 | 10/2011 | Sargand |
| 2011/0272337 A1 | 11/2011 | Palmer |
| 2011/0272352 A1 | 11/2011 | Braig |
| 2011/0297593 A1 | 12/2011 | Kelly |
| 2011/0315611 A1 | 12/2011 | Fulkerson |
| 2011/0315632 A1 | 12/2011 | Freije |
| 2012/0016228 A1 | 1/2012 | Kroh |
| 2012/0018377 A1 | 1/2012 | Tsukamoto |
| 2012/0083729 A1 | 4/2012 | Childers |
| 2012/0085707 A1 | 4/2012 | Beiriger |
| 2012/0092025 A1 | 4/2012 | Volker |
| 2012/0095402 A1 | 4/2012 | Lande |
| 2012/0115248 A1 | 5/2012 | Ansyln |
| 2012/0220528 A1 | 8/2012 | VanAntwerp |
| 2012/0248017 A1 | 10/2012 | Beiriger |
| 2012/0258545 A1 | 10/2012 | Ash |
| 2012/0258546 A1 | 10/2012 | Marran |
| 2012/0273354 A1 | 11/2012 | Orhan et al. |
| 2012/0273415 A1 | 11/2012 | Gerber |
| 2012/0273420 A1 | 11/2012 | Gerber |
| 2012/0277546 A1 | 11/2012 | Soykan |
| 2012/0277551 A1 | 11/2012 | Gerber |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2012/0303079 A1 | 11/2012 | Mahajan |
| 2013/0006128 A1 | 1/2013 | Olde et al. |
| 2013/0018095 A1 | 1/2013 | Vath |
| 2013/0019179 A1 | 1/2013 | Zhao |
| 2013/0020237 A1 | 1/2013 | Wilt et al. |
| 2013/0023812 A1 | 1/2013 | Hasegawa et al. |
| 2013/0025357 A1 | 1/2013 | Noack et al. |
| 2013/0027214 A1 | 1/2013 | Eng |
| 2013/0028809 A1 | 1/2013 | Barton |
| 2013/0030347 A1 | 1/2013 | Sugioka |
| 2013/0030348 A1 | 1/2013 | Lauer |
| 2013/0030356 A1 | 1/2013 | Ding |
| 2013/0037142 A1 | 2/2013 | Farrell |
| 2013/0037465 A1 | 2/2013 | Heyes |
| 2013/0056418 A1 | 3/2013 | Kopperschmidt et al. |
| 2013/0072895 A1 | 3/2013 | Kreischer et al. |
| 2013/0075314 A1 | 3/2013 | Nikolic |
| 2013/0087210 A1 | 4/2013 | Brandl et al. |
| 2013/0110028 A1 | 5/2013 | Bachmann et al. |
| 2013/0116578 A1 | 5/2013 | An |
| 2013/0199998 A1 | 8/2013 | Kelly |
| 2013/0213890 A1 | 8/2013 | Kelly |
| 2013/0213891 A1 | 8/2013 | Karoor |
| 2013/0228516 A1 | 9/2013 | Jonsson |
| 2013/0274642 A1 | 10/2013 | Soykan |
| 2013/0324915 A1 | 12/2013 | (Krensky)Britton |
| 2013/0330208 A1 | 12/2013 | Ly |
| 2013/0331774 A1 | 12/2013 | Farrell |
| 2014/0001112 A1 | 1/2014 | Karoor |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0110340 A1 | 4/2014 | White |
| 2014/0110341 A1 | 4/2014 | White |
| 2014/0138294 A1 | 5/2014 | Fulkerson |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0190885 A1 | 7/2014 | Meyer |
| 2014/0190886 A1 | 7/2014 | Pudil |
| 2014/0190891 A1 | 7/2014 | Lura |
| 2014/0217028 A1 | 8/2014 | Pudil |
| 2014/0217030 A1 | 8/2014 | Meyer |
| 2014/0220699 A1 | 8/2014 | Pudil |
| 2014/0251908 A1 | 9/2014 | Ding |
| 2014/0262812 A1 | 9/2014 | Longhenry |
| 2014/0326671 A1 | 11/2014 | Kelly |
| 2014/0336568 A1 | 11/2014 | Wong |
| 2015/0057602 A1 | 2/2015 | Mason |
| 2015/0108069 A1 | 4/2015 | Merchant |
| 2015/0114891 A1 | 4/2015 | Meyer |
| 2015/0144539 A1 | 5/2015 | Pudil |
| 2015/0144542 A1 | 5/2015 | Pudil |
| 2015/0157960 A1 | 6/2015 | Pudil |
| 2015/0238673 A1 | 8/2015 | Gerber |
| 2015/0250937 A1 | 9/2015 | Pudil |
| 2015/0251161 A1 | 9/2015 | Pudil |
| 2015/0251162 A1 | 9/2015 | Pudil |
| 2015/0258266 A1 | 9/2015 | Merchant |
| 2015/0306292 A1 | 10/2015 | Pudil |
| 2015/0367051 A1 | 12/2015 | Gerber |
| 2015/0367052 A1 | 12/2015 | Gerber |
| 2015/0367055 A1 | 12/2015 | Pudil |
| 2015/0367056 A1 | 12/2015 | Gerber |
| 2015/0367057 A1 | 12/2015 | Gerber |
| 2015/0367058 A1 | 12/2015 | Gerber |
| 2015/0367059 A1 | 12/2015 | Gerber |
| 2015/0367060 A1 | 12/2015 | Gerber |
| 2016/0236188 A1 | 8/2016 | Menon |

(56) References Cited

U.S. PATENT DOCUMENTS

| | | | |
|---|---|---|---|
| 2016/0243299 A1 | 8/2016 | Menon | |
| 2016/0243540 A1 | 8/2016 | Menon | |
| 2016/0243541 A1 | 8/2016 | Menon | |
| 2017/0087533 A1 | 3/2017 | Hobot | |
| 2018/0221852 A1 | 8/2018 | Pudil | |

FOREIGN PATENT DOCUMENTS

| | | |
|---|---|---|
| CN | 102762268 | 10/2012 |
| CN | 103402563 A | 11/2013 |
| CN | 103747818 | 4/2014 |
| CN | 103889478 | 6/2014 |
| CN | 104936633 | 9/2015 |
| CN | 105992599 | 5/2016 |
| CN | 105658326 A | 6/2016 |
| CN | 106413878 A | 2/2017 |
| DE | 3110128 A1 | 9/1982 |
| DE | 102011052188 | 1/2013 |
| EP | 0266795 A2 | 11/1987 |
| EP | 0264695 | 4/1988 |
| EP | 0614081 A1 | 10/1993 |
| EP | 1085295 | 11/2001 |
| EP | 711182 B1 | 6/2003 |
| EP | 1364666 A1 | 11/2003 |
| EP | 0906768 B1 | 2/2004 |
| EP | 1701752 A2 | 9/2006 |
| EP | 1450879 | 10/2008 |
| EP | 1991289 | 11/2008 |
| EP | 1592494 B1 | 6/2009 |
| EP | 2100553 A1 | 9/2009 |
| EP | 2575827 A2 | 12/2010 |
| EP | 2576453 A2 | 12/2011 |
| EP | 2446908 | 5/2012 |
| EP | 2701580 | 11/2012 |
| EP | 2701595 | 11/2012 |
| EP | 1545652 B1 | 1/2013 |
| EP | 1684625 B1 | 1/2013 |
| EP | 2142234 B1 | 1/2013 |
| EP | 2550984 A1 | 1/2013 |
| EP | 1345856 B1 | 3/2013 |
| EP | 1938849 B1 | 3/2013 |
| EP | 2219703 B1 | 3/2013 |
| EP | 2564884 A1 | 3/2013 |
| EP | 2564885 A1 | 3/2013 |
| EP | 2344220 B1 | 4/2013 |
| EP | 1345687 | 6/2013 |
| EP | 2701596 | 3/2014 |
| EP | 2950836 | 12/2015 |
| EP | 3546042 | 10/2019 |
| EP | 3626280 | 3/2020 |
| JP | S5070281 A | 6/1975 |
| JP | S51-55193 | 5/1976 |
| JP | S51-131393 | 11/1976 |
| JP | S61164562 | 7/1986 |
| JP | 2981573 | 11/1999 |
| JP | 2005511250 | 4/2005 |
| JP | H4-90963 | 5/2005 |
| JP | 2007-44602 A | 2/2007 |
| JP | 200744602 | 2/2007 |
| JP | 200744602 A | 2/2007 |
| JP | 5-99464 | 10/2012 |
| JP | 2013502987 | 10/2013 |
| WO | 9106326 A1 | 5/1991 |
| WO | 953201 | 11/1995 |
| WO | 9937342 | 7/1999 |
| WO | 2000038591 A2 | 7/2000 |
| WO | 0057935 | 10/2000 |
| WO | 200066197 A1 | 11/2000 |
| WO | 200170307 A1 | 9/2001 |
| WO | 2001085295 A2 | 9/2001 |
| WO | 0185295 A2 | 11/2001 |
| WO | 2002043859 | 6/2002 |
| WO | 2003043677 A2 | 5/2003 |
| WO | 2003043680 | 5/2003 |
| WO | WO 2003041764 | 5/2003 |
| WO | 2003051422 A2 | 6/2003 |
| WO | 2004008826 | 1/2004 |
| WO | 2004009156 | 1/2004 |
| WO | 2004030716 A2 | 4/2004 |
| WO | 2004030717 A2 | 4/2004 |
| WO | 2004064616 A2 | 8/2004 |
| WO | 2004062710 A3 | 10/2004 |
| WO | WO 2005/062973 A3 | 7/2005 |
| WO | 2005123230 | 12/2005 |
| WO | 2007089855 A2 | 8/2007 |
| WO | WO 20070103411 | 9/2007 |
| WO | 2008075951 A1 | 6/2008 |
| WO | 2009026603 | 12/2008 |
| WO | 2009064984 | 5/2009 |
| WO | 2009157877 A1 | 12/2009 |
| WO | 2009157878 A1 | 12/2009 |
| WO | 20090157877 | 12/2009 |
| WO | 2010028860 | 3/2010 |
| WO | 2010102190 A4 | 11/2010 |
| WO | 2010141949 | 12/2010 |
| WO | WO 2011/017215 | 2/2011 |
| WO | 2011025705 A | 3/2011 |
| WO | 2012148781 | 11/2012 |
| WO | 2012148786 | 11/2012 |
| WO | 2012148789 | 11/2012 |
| WO | 2012162515 A2 | 11/2012 |
| WO | 2012172398 | 12/2012 |
| WO | 2013019179 | 2/2013 |
| WO | 2013019994 A2 | 2/2013 |
| WO | 2013022024 A1 | 2/2013 |
| WO | 2013022837 A1 | 2/2013 |
| WO | 2013025844 | 2/2013 |
| WO | 2013025957 | 2/2013 |
| WO | 2013027214 | 2/2013 |
| WO | 2013028809 | 2/2013 |
| WO | WO 2013/019179 | 2/2013 |
| WO | WO 2013/019994 | 2/2013 |
| WO | WO 2013-025957 | 2/2013 |
| WO | WO 2013-028809 | 2/2013 |
| WO | WO 2013/028809 | 2/2013 |
| WO | WO 2013019179 | 2/2013 |
| WO | WO2014121238 A1 | 2/2013 |
| WO | 2013030642 A1 | 3/2013 |
| WO | 2013030643 A1 | 3/2013 |
| WO | 2012060700 | 5/2013 |
| WO | 2013101888 | 7/2013 |
| WO | 2013103607 A1 | 7/2013 |
| WO | 2013103906 | 7/2013 |
| WO | WO 2013/103607 | 7/2013 |
| WO | WO 2013109922 | 7/2013 |
| WO | 2013114063 A1 | 8/2013 |
| WO | 2013121162 A1 | 8/2013 |
| WO | 14066254 | 5/2014 |
| WO | 14066255 | 5/2014 |
| WO | 14077082 | 5/2014 |
| WO | 2014121162 | 8/2014 |
| WO | 2014121163 | 8/2014 |
| WO | 2014121167 | 8/2014 |
| WO | 2014121169 | 8/2014 |
| WO | 2015060914 | 4/2015 |
| WO | WO 2015/080895 | 4/2015 |
| WO | WO 2015060914 | 4/2015 |
| WO | WO 2015/126879 | 8/2015 |
| WO | 2015142624 | 9/2015 |
| WO | 2015199764 | 12/2015 |
| WO | 2015199765 | 12/2015 |
| WO | 2015199863 | 12/2015 |
| WO | 2015199864 | 12/2015 |
| WO | WO 2015-199863 | 12/2015 |
| WO | WO 2015-199864 | 12/2015 |
| WO | WO 2015199765 | 12/2015 |
| WO | WO 2016/191039 | 12/2016 |
| WO | WO 2016/191041 | 12/2016 |

OTHER PUBLICATIONS

Office Action in U.S. Appl. No. 13/586,824 dated Dec. 21, 2015.
Office Action in U.S. Appl. No. 13/586,824 dated Jun. 4, 2015.

(56) References Cited

OTHER PUBLICATIONS

Eureopean Search Report for App. No. EP14745643 dated Oct. 6, 2016.
PCT/US15/18587 International Preliminary Report on Patentability dated Jun. 6, 2016.
European Search Opinion for App. No. EP12826180 dated Mar. 19, 2015.
European Search Opinion for App. No. EP12826180 dated Jan. 18, 2016.
Khanna, Ramesh, R.T. Krediet, and Karl D. Nolph. Nolph and Gokals Textbook of Peritoneal Dialysis New York: Springer 2009. Print.
Ruperez et al., Comparison of a tubular pulsatile pump and a volumetric pump for continuous venovenous renal replacement therapy in a pediatric animal model, 51 ASAIO J. 372, 372-375 (2005).
St. Peter et al., Liver and kidney preservation by perfusion, 359 The Lancet 604, 606(2002).
Dasselaar et al., Measurement of relative blood volume changes during hemodialysis: merits and limitations, 20 Nephrol Dial Transpl. 2043, 2043-2044 (2005).
Ralph T. Yang, Adsorbents: Fundamentals and Applications 109 (2003).
Henny H. Billett, Hemoglobin and Hematocrit, in Clinical Methods: The History, Physical, and Laboratory Examinations 719(HK Walker, WD Hall, & JW Hurst ed., 1990).
Office Action in App. No. 13/565, 733 dated Jan. 11, 2016.
Office Action in App. No. 13/565, 733 dated Jun. 11, 2015.
Office Action in U.S. Appl. No. 13/757,792 dated Jun. 2, 2016.
Office Action in U.S. Appl. No. 13/757,796 dated Apr. 13, 2015.
Office Action in U.S. Appl. No. 13/757,796 dated Dec. 21, 2015.
Office Action in U.S. Appl. No. 13/835,735 dated Oct. 13, 2015.
Office Action in U.S. Appl. No. 13/836,079 dated Apr. 17, 2015.
Office Action in U.S. Appl. No. 13/836,079 dated Jun. 30, 2016.
Office Action in U.S. Appl. No. 13/791,755 dated Mar. 16, 2016.
Office Action in U.S. Appl. No. 13/791,755 dated Aug. 9, 2016.
Office Action in U.S. Appl. No. 13/835,735 dated Jun. 16, 2016.
Office Action in U.S. Appl. No. 13/836,079 dated Nov. 6, 2015.
Office Action in App. No. AU 2015280604 dated Apr. 8, 2016.
International Search Report from International Application No. PCT/US2014/014347 dated May 9, 2014.
PCT/US2016/030319 Written Opinion dated Jul. 27, 2016.
PCT/US2016/030320 Written Opinion dated Jul. 27, 2016.
PCT/US2012/014347, International Search Report.
PCT/US2015/016273 International Search Report and Written Opinion dated Jun. 9, 2015.
Wester et al., A regenerable postassium and phosphate sorbent system to enhance dialysis efficacy and device portability: an in vitro study Nephrol Dial Transplant (2013) 28: 2364-2371 Jul. 3, 2013.
Office Action in App. No. JP 2016-515476 dated Dec. 26, 2016.
Japanese Patent Publication No. S50-70281A.
PCT/US2015/032494 Written Opinion dated Nov. 19, 2015.
PCT/US2015/032494 International Search Report dated Nov. 19, 2015.
PCT/US2015/019901 International Preliminary Report on Patentability dated May 27, 2016.
[NPL608] PCT/US2015/019901 Written Opinion mailed May 27, 2016.
PCT/US2015/019901 Written Opinion dated Jun. 5, 2015.
PCT/US2015/019901 International Search Report dated Jun. 5, 2015.
PCT/US2015/032485 International Preliminary Report on Patentability dated May 11, 2016.
PCT/US20115/032485 International Preliminary Report on Patentability dated May 11, 2016.
PCT/US2016/030304 International Search Report dated Jul. 27, 2016.
PCT/US2016/030304 Written Opinion dated Jul. 27, 2016.
PCT/US2016/030312 Written Opinion dated Jul. 28, 2016.
PCT/US2016/030312 International Search Report dated Jul. 28, 2016.
PCT/US2016/030319 International Search Report dated Jul. 27, 2016.
PCT/US2016/030320 Written Opinion dated Jul. 28, 2016.
PCT/US2016/030320 International Search Report dated Jul. 28, 2016.
PCT/US2015/032485 Written Opinion dated Oct. 16, 2015.
PCT/US2015/032485 Written Opinion dated Oct. 16, 2016.
PCT/US2015/032485 International Search Report and Written Opinion dated Oct. 16, 2015.
PCT/US2016/030320 International Preliminary Report on Patentability, dated Apr. 20, 2017.
International Preliminary Report from International Application No. PCT/US2014/014348 dated Jan. 9, 2015.
European Search Report from European Application No. EP 14746193.3 dated Oct. 19, 2016.
European Search Report from European Application No. EP 14746193.3 dated Jun. 8, 2016.
PCT/US2014/014345 Written Opinion dated Jun. 24, 2015.
PCT/US2014/014345 International Search Report and Written Opinion dated May 30, 2014.
Office Action in European Application No. 14746428.03 dated Feb. 8, 2017.
European Search Report in European Application No. 14746428.03 dated Aug. 25, 2016.
PCT/US2014/014346 Writtent Opinion dated Apr. 10, 2015.
PCT/US2014/014346 International Search Report and Writtent Opinion dated May 23, 2014.
EP 14746415.0 European Search Report dated Aug. 22, 2016.
Office Action in European Application No. EP 14746415.0 dated Apr. 19, 2017.
Office Action in European Application No. 14746415.0 dated Apr. 19, 2017.
U.S. Appl. No. 13/424,490, published Nov. 1, 2012.
PCT/US2015/020047 International Search Report and Written Opinion dated Jun. 29, 2015.
PCT/US2015/020047 International Preliminary Report on Patentability dated Jun. 30, 2015.
PCT/US2015/020044 Written Opinion dated Jun. 21, 2016.
PCT/US2015/020044 International Preliminary Report on Patentability dated Nov. 4, 2016.
PCT/US2015/020044 International Search Report dated Jun. 30, 2015.
US2015/019881 Written Opinion dated Jun. 16, 2016.
US2015/019881 Written Opinion dated May 9, 2016.
U.S. Appl. No. 13/424,517, dated Nov. 1, 2012.
US2015/019881 International Search Report and Written Opinion dated Jun. 29, 2015.
PCT/US2014/065950 International Preliminary Report on Patentability dated Oct. 28, 2015.
PCT/US2015/032485 Written Opinion dated May 9, 2016.
PCT/US2015/032492 Written Opinion dated Nov. 19, 2015.
PCT/US2015/019901 International Search Report and Written Opinion dated Jun. 5, 2015.
PCT/US2015/032494 International Preliminary Report on Patentablity dated Dec. 27, 2016.
Office Action for Chinese Application No. 201580009562.5 dated Jul. 3, 2017.
International Preliminary Report on Patentability for Application No. PCT/US2015/032492 dated Jun. 30, 2017.
Office Action in European Application No. 14746193.3 dated Apr. 19, 2017.
International Preliminary Report on Patentability for Application No. PCT/US2015/016273 dated Feb. 19, 2016.
European Search Report for App. No. 15751391.2 dated Aug. 4, 2017.
European Search Report and supplementary Search Report for App. No. 14865374.4 dated Jun. 12, 2017.
European Search Report and Supplemental Search Report in European Application No. 14865374.4 dated Jun. 12, 2017.
PCT/US2015/020046 International Search Report and Written Opinion dated Jun. 29, 2015.

(56) References Cited

OTHER PUBLICATIONS

PCT/US2015/020044 International Search Report Written Opinion dated Jun. 30, 2015.
Nedelkov, et. al., Design of buffer exchange surfaces and sensor chips for biosensor chip mass spectrometry, Proteomics, 2002, 441-446,2(4).
European Search Report App 14865374.4, dated Jun. 12, 2017.
Chinese Office Action for App. No. 201711179516.7, dated Feb. 19, 2020.
Chinese Office Action for App. No. 201711179528.X, dated Jul. 27, 2020.
U.S. Appl. No. 13/757,693, filed Feb. 1, 2013, Medtronic.
U.S. Appl. No. 13/757,709, filed Feb. 1, 2013, Medtronic.
U.S. Appl. No. 13/757,728, filed Feb. 1, 2013, Medtronic.
U.S. Appl. No. 13/836,538, filed Mar. 15, 2013, Medtronic.
U.S. Appl. No.61/760,033, filed Feb. 1, 2013, Medtronic.
Brynda, et. al., The detection of toman 2-microglcbuiin by grating coupler immunosensor with three dimensional antibody networks. Biosensors & Bioelectronics, 1999, 363-368, 14(4).
Wheaton, et al., Dowex Ion Exchange Resins-Fundamentals of Ion Exchange; Jun. 2000, pp. 1-9. http://www.dow.com/scripts/litorder.asp?filepath=liquidseps/pdfs/noreg/177-01837.pdf.
Zhong, et al., Miniature urea sensor based on H(+)-ion sensitive field effect transistor and its application in clinical analysis, Chin. J. Biotechnol., 1992, 57-65. 8(1).
PCT/US2012/034331, International Search Report and Written Opinion dated Jul. 9, 2012.
Roberts M, The regenerative dialysis (REDY) sorbent system. Nephrology, 1998, 275-278:4.
U.S. Appl. No. 61/480,544, dated Apr. 29, 2011.
U.S. Appl. No. 61/480,541 dated Apr. 29, 2011.
Hemametrics, Crit-Line Hematocrit Accuracy, 2003, 1-5, vol. 1, Tech Note No. 11 (Rev. D).
Weissman, S., et al., Hydroxyurea-induced hepatitis in human immunodeficiency virus-positive patients. Clin. Infec. Dis, (Jul. 29, 1999): 223-224.
PCT/US2012/034334, International Search Report, dated Jul. 6, 2012.
PCT/US2012/034335, International Search Report, dated Sep. 5, 2012.
PCT/US/2012/034327, International Search Report, dated Aug. 13, 2013.
PCT/US/2012/034329, International Search Report, dated Dec. 3, 2012.
International Search Report from PCT/US2012/051946 dated Mar. 4, 2013.
U.S. Appl. No. 61/526,209.
Wang, Fundamentals of intrathoracic impedance monitoring in heart failure, Am. J. Cardiology, 2007, 3G-10G: Suppl.
PCT/US2014/067650 International Search Report Written Opinion dated Mar. 9, 2015.
Bleyer, et. al., Sudden and cardiac death rated in hemodialysis patients, Kidney International. 1999, 1553-1559: 55.
PCT/US2012/034333, International Preliminary Report on Patentability, dated Oct. 29, 2013.
PCT/US2012/034333, International Search Report, dated Aug. 29, 2012.
PCT/US2014/065950 International Search Report and Written Opinion dated Feb. 24, 2015.
Culleton, Bf et al. Effect of Frequent Nocturnal Hemodialysis vs. Conventional Hemodialysis on Left Ventricular Mass and Quality of Life. 2007 Journal of the American Medical Association 298 (11), 1291-1299.
Redfield, et. al., Restoration of renal response to atria! natriuretic factor in experimental low-output heat failure, Am. J. Physiol., Oct. 1, 1989, R917-923:257.
Rogoza, et. al., Validation of A&D UA-767 device for the self-measurement of blood pressure, Blood Pressure Monitoring, 2000, 227-231, 5(4).
Lima, et. al., An electrochemical sensor based on nanostructure hollsndite-type manganese oxide for detection of potassium ion, Sensors, Aug. 24, 2009, 6613-8625, 9.
MacLean, et, al., Effects of hindlimb contraction on pressor and muscle interstitial metabolite responses in the cat, J. App. Physiol., 1998, 1583-1592, 85(4).
PCT Application, PCT/US2013/020404, filed Jan. 4, 2013.
PCT/US2014/014346 International Search Report and Written Opinion.
PCT/US2014/014345 International Search Report and Written Opinion, dated May 2014.
PCT/US2014/014357 International Search Report and Written Opinion dated May 19, 2014.
Ronco et al. 2008, Cardiorenal Syndrome, Journal American College Cardiology, 52:1527-1539, Abstract.
Overgaard, et. al., Activity-induced recovery of excitability in K+-depressed rat soleus muscle, Am. J. p. 280: R48-R55, Jan. 1, 2001.
Overgaard et. al., Relations between excitability and contractility in rate soleusmuscle: role of the NA+-K+ pump and NA+-K-S gradients. Journal of Physiology, 1999, 215-225, 518(1).
PCT/US2015/032492 International Search Report dated Nov. 19, 2015.
Coast, et al. 1990, An approach to Cardiac Arrhythmia analysis Using Hidden Markov Models, IEEE Transactions on Biomedical Engineering. 1990, 37(9):826-835.
Secemsky, et al., High prevalence of cardiac autonomic dysfunction and T-wave alternans in dialysis patients. Heart Rhythm, Apr. 2011, 592-598: vol. 8, No. 4.
Wei, et. al., Fullerene-cryptand coated piezoelectric crystal urea sensor based on urease, Analytics Chimica Acta, 2001,77-85:437.
Gambro AK 96 Dialysis Machine Operators Manual, Dec. 2012. p. 1-140.
Gambro AK 96 Dialysis Machine Operators Manual, Dec. 2012. p. 141-280.
Gambro AK 96 Dialysis Machine Operators Manual, Dec. 2012. p. 281-420.
Gambro AK 96 Dialysis Machine Operators Manual, Dec. 2012. p. 421-534.
Leifer et al., A Study on the Temperature Variation of Rise Velocity for Large Clean Bubbles, J. Atmospheric & Oceanic Tech., vol. 17, pp. 1392-1402, Oct. 2000.
Talaia, Terminal Velocity of a Bubble Rise in a Liquid Column World Acad. of Sci., Engineering & Tech., vol. 28, pp. 264-268, Published Jan. 1, 2007.
The FHN Trial Group. In-Center. Hemodialysis Six Times per Week versus Three Times per Week, New England Journal of Medicine, 2010 Abstract.
Gotch FA, Sargent JA A mechanistic analysis of the National Cooperative Dialysis Study (NCDS). Kidney int. 1985: 28:526-34.
Daugirdas JT. Second generation logarithmic estimates of single-pool variable volume Kt/V and analysis of error. J Am Soc Nephrol, 1993:4:1205-13.
Steil et al. Intl Journ Artif Organs, 1993, In Vivo Verification of an Automatic Noninvasive System for Real Time Kt Evaluation, ASAIO J., 1993, 39:M348-52.
PCT/US2012/034332, International Search Report, dated Jul. 5, 2012.
Siegenthaler, et al., Pulmonary fluid status monitoring with intrathoracic impedance, Journal of Clinical Monitoring and Computing, 24:449-451, published Jan. 12, 2011.
John Wm Agar: Review: Understanding sorbent dialysis systems, Nephrology, vol. 15, No. 4, Jun. 1, 2010, pp. 406-411.
EP. App. 14746193.3 Search Report dated Oct. 19, 2016.
PCT/US2015/016270 International Search Report and Written Opinion dated Jun. 5, 2015.
Chinese Office Action for App. No. 201711179528.X, dated Mar. 26, 2020.
Chinese Office Action for App. No. 201810580243.5, dated Jul. 3, 2020.
Chinese Office Action in App. No. 201580009563.X, dated Mar. 13, 2018.

(56) References Cited

OTHER PUBLICATIONS

European Search Report for App. No. 15812081.6, dated Mar. 8, 2018.
European Search Report for App. No. 18153940.4, dated Jun. 12, 2018.
European Search Report for App. No. 18153940.4, dated Sep. 28, 2018.
European Search Report for App. No. 19191469.6, dated Jan. 8, 2020.
European Search Report for App. No. 19197167.0, dated Jan. 30, 2020.
European Search Report for App. No. 20158130.3, dated Jul. 8, 2020.
European Search Report for App. No. 20164524.9, dated Aug. 21, 2020.
European Search Report for EP 15811439, dated Feb. 15, 2018.
European Search Report for EP App. No. 15810804.3, dated Feb. 15, 2018.
European Search Report for EP App. No. 15811326.6, dated Feb. 14, 2018.
European Search Report for EP App. No. 15811573.3, dated Feb. 15, 2018.
European Search Report for EP App. No. 15812413.1, dated Feb. 2, 2018.
European Search Report for EP18177673.3-1104 (dated Oct. 19, 2018).
European Search Report for EP18177683.2-1104 (dated Nov. 8, 2018).
European Search Report in EP 15811454, dated Feb. 15, 2018.
European Search Report in EP 15812559.1, dated Jan. 31, 2018.
Office Action for Chinese App. No. 201711179516.7, dated Sep. 11, 2019.
Office Action for Chinese App. No. 201810042927, dated Sep. 23, 2019.
Office Action in Japanese Application No. 2016-553344, dated Apr. 24, 2018.
PCT/US2016/030304_IPRP.
PCT/US2016/030319_IPRP.
Search Report for Brazilian App. No. BR112016019111, dated Mar. 12, 2020.
Search Report for EP App. No. 17203984.4, dated Mar. 29, 2018.
Search Report for European App. No. 19187736.4, dated Dec. 16, 2019.
Search Report in EP App. No. 15752771, dated Nov. 22, 2017.

* cited by examiner

ZIRCONIUM OXIDE MODULE CONDITIONING

CROSS-REFERENCE TO RELATED APPLICATIONS

This application claims priority to U.S. application Ser. No. 15/798,233 filed Oct. 30, 2017, which claims the benefit of and priority to U.S. Provisional Patent Application No. 62/427,806 filed Nov. 29, 2016, the entire disclosures of each of which are incorporated by reference herein.

FIELD OF THE INVENTION

The invention relates to devices, systems, and methods for conditioning a zirconium oxide sorbent module for use in dialysis after recharging. The devices, systems, and methods can provide for conditioning and recharging of zirconium oxide in a single system, or in separate systems.

BACKGROUND

Zirconium oxide is used in sorbent dialysis to remove anionic wastes from dialysate and to capture phosphate ions that may bleed out of a zirconium phosphate sorbent material. Generally, after use, the zirconium oxide is discarded and replaced. Because zirconium oxide is expensive and rechargeable, sorbent reprocessors can treat the zirconium oxide with strong base solutions to enable reuse of the zirconium oxide material.

For reprocessing, zirconium oxide is generally removed from a sorbent cartridge, separated from other sorbent materials, treated with strong base, and then placed into a new sorbent cartridge. The known reprocessing is costly and labor intensive.

Zirconium oxide treated with strong base will consume total carbonate if used in dialysis, resulting in a basic solution unsafe for patients. Further, to simplify bicarbonate control during dialysis, the zirconium oxide and zirconium phosphate should be in an equilibrium state.

Hence, there is a need for systems and methods to condition recharged zirconium oxide to place the zirconium oxide in a state for use in dialysis. There is a further need for systems and methods that can recharge and condition the zirconium oxide within a sorbent module. There is an additional need for systems and methods to condition a recharged zirconium oxide module to an equilibrium state with a zirconium phosphate module for later use in dialysis.

SUMMARY OF THE INVENTION

The first aspect of the invention relates to a method of conditioning zirconium oxide in a zirconium oxide module. In any embodiment, the method can include the steps of pumping a conditioning solution through the zirconium oxide module in a flow path to condition the zirconium oxide module wherein the conditioning solution has sodium bicarbonate at a desired zirconium oxide effluent pH.

In any embodiment, the method can include the step of recharging the zirconium oxide in the zirconium oxide module prior to conditioning the zirconium oxide module by pumping a base solution through the zirconium oxide module.

In any embodiment, the method can include the step of pumping the conditioning solution through a zirconium phosphate module prior to pumping the conditioning solution through the zirconium oxide module.

In any embodiment, the flow path can be a dialysate flow path including the zirconium phosphate module and zirconium oxide module.

In any embodiment, the flow path can be a recharging flow path including the zirconium phosphate module and zirconium oxide module.

In any embodiment, the desired zirconium oxide effluent pH can be between 5.0 and 7.5.

In any embodiment, the method can include the step of generating the conditioning solution in the flow path.

In any embodiment, the step of generating the conditioning solution can include mixing a sodium bicarbonate solution with acid.

In any embodiment, the step of generating the conditioning solution can include mixing a sodium bicarbonate solution with carbon dioxide.

In any embodiment, the conditioning solution can be pumped through the zirconium oxide module for between 5-30 minutes.

In any embodiment, a volume of the conditioning solution pumped through the zirconium oxide module can be between 0.5 and 20 L.

In any embodiment, the method can include the step of disinfecting the zirconium oxide sorbent module by pumping a disinfectant solution through the zirconium oxide sorbent module.

In any embodiment, the step of generating the conditioning solution can comprise pumping a fluid in a dialysate flow path through a first sorbent module; the first sorbent module containing a solid sodium bicarbonate.

The features disclosed as being part of the first aspect of the invention can be in the first aspect of the invention, either alone or in combination, or follow a preferred arrangement of one or more of the described elements.

The second aspect of the invention is drawn to a system. In any embodiment the system can include a recharging flow path having at least one receiving compartment for receiving a zirconium oxide module; the at least one receiving compartment having a zirconium oxide module inlet and a zirconium oxide module outlet; a base source fluidly connected to the recharging flow path; a bicarbonate source fluidly connected to the recharging flow path; a pump for pumping fluid from the base source and the bicarbonate source through the zirconium oxide module.

In any embodiment, the system can include an acid source fluidly connected to the recharging flow path.

In any embodiment, the system can include a static mixer in the recharging flow path; wherein the static mixer is fluidly connected to the acid source and the bicarbonate source.

In any embodiment, the system can include a carbon dioxide source fluidly connected to the recharging flow path.

In any embodiment, the carbon dioxide source can be fluidly connected to the bicarbonate source by a fluid connector.

In any embodiment, the system can include a pressure sensor on the fluid connector.

In any embodiment, the system can include a pH sensor in the recharging flow path.

In any embodiment, the system can include at least a second receiving compartment in the recharging flow path for receiving a zirconium phosphate module; the second receiving compartment having a zirconium phosphate module inlet and a zirconium phosphate module outlet and a fluid connector connecting zirconium phosphate module outlet to the zirconium oxide module inlet.

In any embodiment, the system can include an acid source, a brine source, or combinations thereof, fluidly connected to the zirconium phosphate module inlet.

The features disclosed as being part of the second aspect of the invention can be in the second aspect of the invention, either alone or in combination, or follow a preferred arrangement of one or more of the described elements.

DETAILED DESCRIPTION OF THE INVENTION

Figure 1:
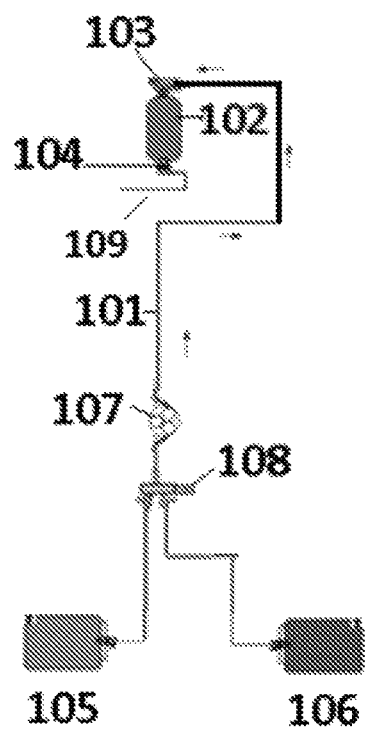
FIG. 1 shows a flow path for recharging and conditioning a zirconium oxide module.

Unless defined otherwise, all technical and scientific terms used have the same meaning as commonly understood by one of ordinary skill in the art.

The articles "a" and "an" are used to refer to one or to over one (i.e., to at least one) of the grammatical object of the article. For example, "an element" means one element or over one element.

An "acid" as used can be a Lewis acid or a Brønsted-Lowry acid. A Lewis acid is capable of accepting a lone pair of electrons. A Brønsted-Lowry acid is capable of donating a hydrogen ion to another compound.

An "acid source" is a fluid or concentrate source from which an acidic solution can be obtained.

The term "base solution" refers to any aqueous solution containing hydroxide ions and a pH of greater than 7.0.

A "base source" is a fluid or concentrate source from which a base solution can be obtained.

The term "bicarbonate source" refers to a source of bicarbonate ions in solid and/or solution form. The bicarbonate ions can be present as a bicarbonate salt of any type. The bicarbonate source can contain at least one fluid pathway and include components such as conduits, valves, filters or fluid connection ports, any of which are fluidly connectable to each other or to a fluid flow path. The bicarbonate source can either be formed as a stand-alone enclosure or a compartment integrally formed with an apparatus containing the bicarbonate source.

A "brine source" is a fluid or concentrate source from which a brine solution can be obtained. As used herein, a brine solution can refer to any solution comprising acids, bases and/or salts.

A "carbon dioxide source" refers to a reservoir, a pressurized cylinder, or tank containing carbon dioxide gas.

The term "comprising" includes, but is not limited to, whatever follows the word "comprising." Use of the term indicates the listed elements are required or mandatory but that other elements are optional and may be present.

The terms "conditioning" or "to condition" refer to processes designed to allow safe and effective use of a component in dialysis.

A "conditioning solution," as used herein, is a solution containing bicarbonate ions for use in conditioning a zirconium oxide module.

A "connector" and "for connection" describe the concept of forming a fluid connection between two components wherein fluid, gas, or mixture of both gas and fluid can flow from one component, through a connector or a component for connection, to another component. The connector provides for a fluid connection in its broadest sense and can include any type of tubing, fluid or gas passageway, or conduit between any one or more components of the invention. The connection can optionally be disconnected and then reconnected.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

A "control system" can be a combination of components that act together to maintain a system to a desired set of performance specifications. The control system can use processors, memory and computer components configured to interoperate to maintain the desired performance specifications. The control system can also include fluid or gas control components, and solute control components as known within the art to maintain the performance specifications.

The term "desired zirconium oxide effluent pH" refers to a preferred pH range for fluid exiting a zirconium oxide module during dialysis.

The terms "determining" and "determine" refer to ascertaining a particular state or desired state of a system or variable(s).

A "dialysate flow path" is a route in which a fluid will travel during dialysis.

The term "disinfectant solution" refers to any solution capable of destroying or removing bacterial contaminants from a reusable sorbent module.

The terms "disinfecting," "disinfected," or to "disinfect" refer to removing bacterial contaminants from a component or system.

A "flow path" is one or more connectors or components through which fluid can travel.

The term "fluid" can be any substance that has no fixed shape that yields easily to external pressure such as a gas or a liquid. Specifically, the fluid can be water containing any solutes at any concentration.

The term "fluidly connectable," "fluidly connected," and "for fluid connection" refer to the ability to pass fluid or gas from one point to another point. The two points can be within or between any one or more of compartments, modules, systems, components, and rechargers, all of any type. The connection can optionally be disconnected and then reconnected.

A "fluid connector," "fluid connection," and the like describe a connection between two components wherein fluid or gas can flow from one component, through a connector or a component for connection, to another component. The connector provides for a fluid connection in its broadest sense and can include any type of tubing, fluid or gas passageway, or conduit between any one or more components of the invention. The connection can optionally be disconnected and then reconnected.

The terms "generating" or "to generate" refer to creating a fluid with a specified concentration, pH, temperature, and/or volume from one or more fluid sources.

The term "mixing" or "to mix" generally refers to causing two or more fluids from any source to combine together. For example, "mixing" can include turbulent flow at a location in a fluid line or a junction. Another example of "mixing" can include receiving one or more fluids in a component configured to receive fluids from one or multiple sources and to mix the fluids together in the component. Yet another example of "mixing" includes one or more fluids used in dissolution of one or more solid components to be dissolved in one or more fluids.

A "module inlet" is a connector through which a fluid, slurry, or aqueous solution can enter a sorbent module.

A "module outlet" is a connector through which a fluid, slurry, or aqueous solution can exit a sorbent module.

The term "pH sensor" refers to a device for measuring the pH or $H^+$ concentration of a liquid in a vessel, container, or fluid line.

The term "pressure sensor" refers to a device for measuring the pressure of a gas or liquid in a vessel, container, or fluid line.

The term "pump" refers to any device that causes the movement of fluids or gases by applying suction or pressure.

The terms "pumping," "pumped," or to "pump" refer to moving a fluid with a pump.

"Recharging" refers to treating a sorbent material to restore the functional capacity of the sorbent material to put the sorbent material back into a condition for reuse or use in a new dialysis session. In some instances, the total mass, weight and/or amount of "rechargeable" sorbent materials remain the same. In some instances, the total mass, weight and/or amount of "rechargeable" sorbent materials change. Without being limited to any one theory of invention, the recharging process may involve exchanging ions bound to the sorbent material with different ions, which in some instances may increase or decrease the total mass of the system. However, the total amount of the sorbent material will in some instances be unchanged by the recharging process. Upon a sorbent material undergoing "recharging," the sorbent material can then be said to be "recharged."

A "recharging flow path" is a path through which fluid can travel while recharging sorbent material in a reusable sorbent module.

A "receiving compartment" is a space within a recharger or other apparatus into which a sorbent module to be recharged is placed.

The term "saturated" refers to a solution containing the greatest amount of a solute under given operating conditions.

The term "solid sodium bicarbonate" refers to sodium bicarbonate in the solid phase, and can include either granular, crystalline, or powdered forms, or combinations thereof, of the sodium bicarbonate.

A "sorbent cartridge module" or "sorbent module" means a discreet component of a sorbent cartridge. Multiple sorbent cartridge modules can be fitted together to form a sorbent cartridge of two, three, or more sorbent cartridge modules. In some embodiments, a single sorbent cartridge module can contain all of the necessary materials for dialysis. In such cases, the sorbent cartridge module can be a "sorbent cartridge."

A sorbent "recharger" is an apparatus designed to recharge at least one sorbent material.

A "static mixer" is a component configured to receive fluids from one or multiple sources and to mix the fluids together. The static mixer may include components that agitate the fluids to further mixing.

"Zirconium oxide", also known as hydrous zirconium oxide, is a sorbent material that removes anions from a fluid, exchanging the removed anions for different anions.

A "zirconium oxide sorbent module" is a sorbent module containing zirconium oxide.

"Zirconium phosphate" is a sorbent material that removes cations from a fluid, exchanging the removed cations for different cations.

A "zirconium phosphate sorbent module" is a sorbent module containing zirconium phosphate.

Zirconium Oxide Conditioning

The invention is drawn to systems and methods for conditioning a zirconium oxide sorbent module after recharging for reuse in dialysis. FIG. 1 illustrates a non-limiting embodiment of a recharger flow path for recharging and conditioning of a zirconium oxide sorbent module 102. The zirconium oxide sorbent module 102 can be placed in a receiving compartment of a recharger and fluidly connected to the recharging flow path 101 through zirconium oxide module inlet 103 and zirconium oxide module outlet 104 into effluent line 109. A base solution containing a strong base, such as sodium hydroxide, can be pumped through the zirconium oxide sorbent module 102 from base source 105 fluidly connected to recharging flow path 101. Pump 107 provides a driving force for pumping the fluids through recharging flow path 101. The hydroxide ions in the base solution will displace phosphate and other anions bound to the zirconium oxide during dialysis. After pumping base solution through the zirconium oxide sorbent module 102, the zirconium oxide will be substantially saturated with hydroxide ions, and in a state that will consume total carbonate from solutions, including $CO_3^{2-}$, $HCO_3^-$ and $CO_2$ gas. The consumption of total carbonate by the zirconium oxide creates a basic dialysate having an unacceptable pH for therapy. To avoid consumption of total carbonate, the zirconium oxide must be conditioned. The conditioning process places the zirconium oxide sorbent module 102 in an appropriate chemical state for reuse in dialysis. Conditioning of the zirconium oxide with sodium bicarbonate places the zirconium oxide in pH equilibrium with the bicarbonate conditioning solution. To condition the zirconium oxide in the zirconium oxide sorbent module 102, bicarbonate solution at a predetermined desired zirconium oxide effluent pH is pumped through the zirconium oxide sorbent module 102 from bicarbonate source 106 fluidly connected to recharging flow path 101. Valve 108 controls the movement of fluid from the base source 105 and bicarbonate source 106 through the recharging flow path 101. One of skill in the art will understand that additional or alternative fluid sources can be included for recharging and conditioning of the zirconium oxide sorbent module 102. A disinfectant source (not shown) containing a disinfectant solution such as bleach, peracetic acid, citric acid, or any other disinfectant known in the art, can be included for disinfecting the zirconium oxide sorbent module 102 prior to reuse. The zirconium oxide sorbent module 102 can be disinfected with bleach, peracetic acid, citric acid, or any other disinfectant by pumping a disinfectant solution through the zirconium oxide sorbent module 102 at the beginning of the recharging and conditioning process, after conditioning and recharging, or in parallel with any of the conditioning or recharging steps. The zirconium oxide sorbent module 102 can be disinfected and recharged in parallel by using a combined base and bleach solution. Alternatively, the zirconium oxide sorbent module 102 can be disinfected and conditioned in parallel by using a combined bicarbonate and bleach solution at the desired zirconium oxide effluent pH. A water source (not shown) can be included for rinsing or flushing the zirconium oxide sorbent module 102 before or after disinfection or recharging or conditioning.

The conditioning solution is pumped through the zirconium oxide sorbent module 102 for a sufficient length of time to ensure complete conditioning. The conditioning solution can be pumped through the zirconium oxide sorbent module 102 for any length of time including between any of 5 and 30 minutes, 5 and 10 minutes, 5 and 8 minutes, 7 and 10 minutes, 8 and 12 minutes, 10 and 15 minutes, 10 and 30 minutes, 15 and 25 minutes, or 20 and 30 minutes.

During dialysis, the zirconium oxide sorbent module 102 is used with zirconium phosphate and other sorbent materials for regeneration of dialysate. To simplify therapy and therapy modeling, equilibration of the zirconium oxide module with the zirconium phosphate is desired. The equilibration of zirconium phosphate and zirconium oxide means the pH of the zirconium oxide and zirconium phosphate effluents during therapy are the same. For example, if a desired zirconium phosphate effluent pH is determined to be 6.5, then the desired zirconium oxide effluent pH can also be 6.5 and the conditioning process can use a bicarbonate solution at a pH of 6.5 to place the zirconium phosphate and zirconium oxide sorbent modules in an equilibrium state. However, the zirconium oxide can be conditioned to any desired zirconium oxide effluent pH by using a bicarbonate solution at the desired zirconium oxide effluent pH.

The bicarbonate in bicarbonate source 106 can include bicarbonate ions in solid and/or solution form. For example, a bicarbonate dry cartridge may be included in bicarbonate source 106. Water can be added to the bicarbonate source 106 to dissolve the bicarbonate in the dry cartridge, or flowed through the dry cartridge, generating a bicarbonate solution of known concentration for use in conditioning. Alternatively, bicarbonate source 106 can include a premade bicarbonate solution.

The concentration of the bicarbonate in bicarbonate source 106 can be any concentration leading to a desired zirconium oxide effluent pH. In certain embodiments, the concentration of bicarbonate used in conditioning the zirconium oxide can be between 0.1 M and saturated, between 0.1 M and 1.0 M, between 0.5 M and 1.0 M, between 0.5 M and 2.0 M, between 1.0 M and saturated, or between 2.0 and saturated. The desired zirconium oxide effluent pH can be any pH, and in a preferred embodiment is between 5.0 and 7.5. In certain embodiments, the desired zirconium effluent pH can be between any of 5.0 and 6.0, between 5.0 and 6.5, between 5.5 and 6.5, between 5.5 and 7.0, between 6.0 and 7.5, or between 6.5 and 7.5. In certain embodiments, the conditioning solution can be heated to a specified temperature while conditioning the zirconium oxide. The conditioning solution can be heated to any temperature between 20 and 100° C., including between 20 and 35° C., between 20 and 50° C., between 40 and 60° C., between 40 and 80° C., between 50 and 75° C., or between 50 and 100° C. Approximately 4 mmoles of bicarbonate per gram of zirconium oxide is necessary for full conditioning of a zirconium oxide sorbent module with a phosphate capacity of about 0.8 mmoles phosphate/g of zirconium oxide. One of ordinary skill in the art will understand more bicarbonate will be necessary for a zirconium oxide module containing more zirconium oxide, or having a higher phosphate capacity. For example, the bicarbonate solution can be a 1M bicarbonate solution at a pH of 6.5, requiring 1.3 L of conditioning solution. At higher concentrations, less conditioning solution will be required. However, because significant carbon dioxide gas will be in equilibrium with the bicarbonate at a pH of around 6.5, a high pressure is required to create a stable 6.5 pH bicarbonate solution at high concentration. If the pressure is not high enough, degassing and release of carbon dioxide will occur. The concentration and volume of the bicarbonate conditioning solution used can be based on the desired zirconium oxide effluent pH and the pressure capabilities of the system. The conditioning solution used can be any volume, including between any of 0.5 and 20.0 L, 0.5 and 1.0 L, 0.75 and 1.25 L, 1.0 and 1.5 L, 1.0 and 5.0 L, 2.5 and 7.5 L, 5.0 and 15.0 L, 5.0 and 20.0 L, or 10.0 and 20.0 L. Although the recharging flow path 101 is illustrated as a flow path for both recharging and conditioning a zirconium oxide sorbent module 102, one of skill in the art will understand that a separate conditioning apparatus can be constructed without base source 105 solely for conditioning of the zirconium oxide sorbent module 102.

Figure 2:
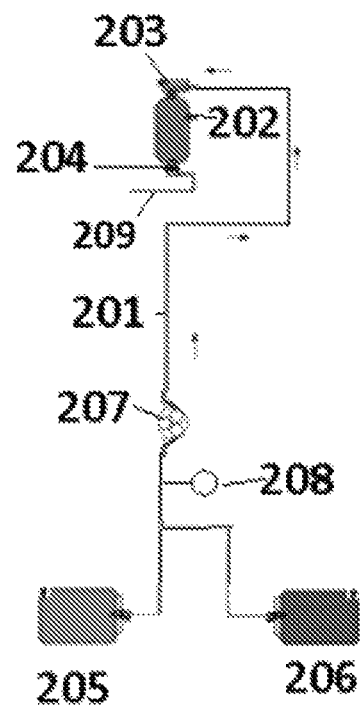
FIG. 2 shows a flow path for generating a conditioning solution from a bicarbonate solution and an acid solution.

The conditioning solution containing sodium bicarbonate at a desired zirconium oxide effluent pH can be provided in a pre-mixed bicarbonate source 106 at the proper pH, as illustrated in FIG. 1. Alternatively, the conditioning solution can be generated by the system. FIG. 2 illustrates a system for generating the conditioning solution. A zirconium oxide sorbent module 202 can be placed in a receiving compartment of a recharger or separate conditioning apparatus and connect to flow path 201 through zirconium oxide sorbent module inlet 203 and zirconium oxide sorbent module outlet 204 into effluent line 209. To generate the conditioning solution, sodium bicarbonate from bicarbonate source 205 can be mixed with an acid from acid source 206. Pump 207 provides a driving force for pumping fluid through the flow path 201. The acid in acid source 206 can be any acid, including acetic acid, hydrochloric acid, or any other acid known in the art. The concentrations of bicarbonate in bicarbonate source 205 and acid in acid source 206 can be set to generate a conditioning fluid having a desired zirconium oxide effluent pH when mixed in flow path 201. A static mixer (not shown) can be included in flow path 201 to ensure mixing of the acid and bicarbonate. Alternatively, the acid and bicarbonate can be mixed through mixing of the fluid streams at the junction between the two lines. A pH sensor 208 ensures the pH of the mixed conditioning solution is within an acceptable range of the desired zirconium oxide effluent pH. Valves (not shown) can be included to control the movement of fluid from the bicarbonate source 205 and acid source 206, allowing a customizable conditioning solution having a variable pH controlled by the relative amounts of bicarbonate and acid used. One of skill in the art will understand a base source (not shown) can be included in the flow path 201 of FIG. 2 for recharging the zirconium oxide sorbent module 202 prior to conditioning in a single system. Alternatively, a separate recharger can recharge the zirconium oxide sorbent module 202, and conditioning carried out with a different apparatus.

Figure 3:
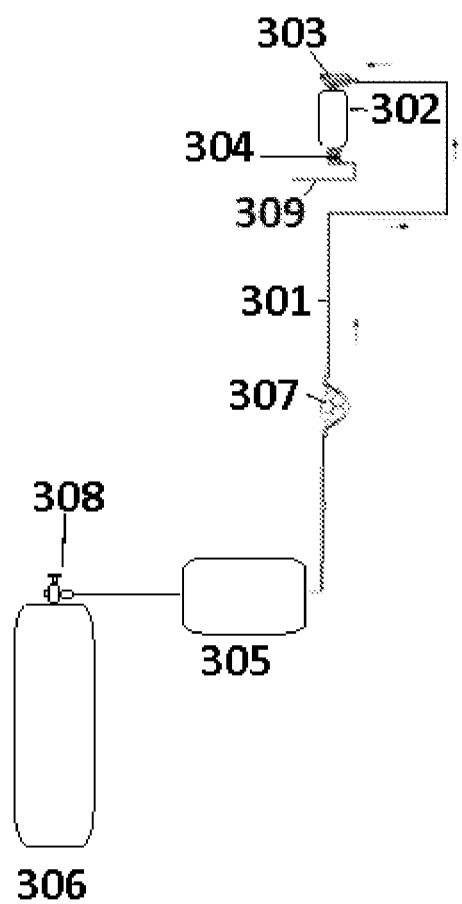
FIG. 3 shows a flow path for generating a conditioning solution from a bicarbonate solution and a carbon dioxide source.

FIG. 3 illustrates an alternative method of generating a conditioning solution using carbon dioxide gas from carbon dioxide source 306. A zirconium oxide sorbent module 302 can be placed in a receiving compartment of a recharger or conditioning apparatus and connect to flow path 301 through zirconium oxide module inlet 303 and zirconium oxide module outlet 304 into effluent line 309. Pump 307 provides a driving force for moving fluid through the flow path 301. A bicarbonate source 305 fluidly connected to flow path 301 can contain a bicarbonate solution at a higher pH. Carbon dioxide gas from carbon dioxide source 306 can be metered into the bicarbonate source 305 through a fluid connector to create a bicarbonate solution having a desired zirconium oxide effluent pH. Pressure regulator 308 controls the flow of carbon dioxide gas to the bicarbonate source 305, allowing control over the pH of the fluid after mixing. A pressure sensor (not shown) ensures the correct pressure of carbon dioxide is delivered to the bicarbonate source 305. A pH sensor (not shown) can ensure the pH of the generated solution is at the desired zirconium oxide effluent pH. One of skill in the art will understand a base source (not shown) can be included in the flow path 301 of FIG. 3 for recharging the zirconium oxide sorbent module 302 prior to conditioning in a single system. Alternatively, a separate recharger can recharge the zirconium oxide sorbent module 302, and conditioning carried out with a different apparatus.

Figure 4:
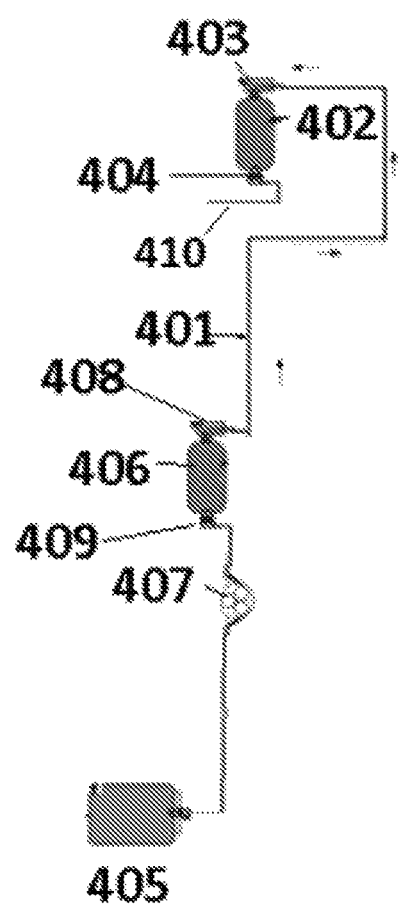
FIG. 4 shows a flow path for generating a conditioning solution from a bicarbonate solution passed through a zirconium phosphate module.

FIG. 4 illustrates a flow path 401 with a zirconium phosphate sorbent module 406 for generating the conditioning solution. The zirconium oxide sorbent module 402 can be placed in a receiving compartment of a recharger or conditioning apparatus and connect to the flow path 401 through zirconium oxide module inlet 403 and zirconium oxide module outlet 404 into effluent line 410. Pump 407 provides a driving force for pumping fluid through the flow path 401. Bicarbonate source 405, fluidly connected to flow path 401, can contain bicarbonate at any pH. A second receiving compartment can receive a zirconium phosphate sorbent module 406. The bicarbonate solution passes through zirconium phosphate sorbent module 406, connected by a fluid connector to the flow path 401 through zirconium phosphate module inlet 409 and zirconium phosphate module outlet 408. The bicarbonate conditioning solution will equilibrate with the zirconium phosphate sorbent module 406, generating a bicarbonate solution with a pH dependent upon the relative amounts of hydrogen and sodium loaded onto the zirconium phosphate sorbent module 406. As such, if the zirconium phosphate sorbent module 406 is the same zirconium phosphate sorbent module used with the zirconium oxide sorbent module 402 in dialysis, or is loaded with hydrogen and sodium ions in the same ratio as the zirconium phosphate sorbent module used in dialysis, then the pH of the conditioning solution exiting zirconium phosphate sorbent module 406 will be at the desired equilibrium pH. One of skill in the art will understand a base source (not shown) can be included in the flow path 401 of FIG. 4 for recharging the zirconium oxide sorbent module 402 prior to conditioning in a single system. Alternatively, a separate recharger can recharge the zirconium oxide sorbent module 402, and conditioning carried out with a different apparatus. The zirconium phosphate sorbent module 406 illustrated in FIG. 4 can be a dedicated zirconium phosphate sorbent module, or a zirconium phosphate sorbent module that will be removed from the flow path 401 and used in subsequent dialysis. A dedicated zirconium phosphate sorbent module can generate the conditioning solution through multiple cycles before being recharged or replaced. Approximately 150 g of zirconium phosphate is necessary for conditioning of a zirconium oxide module. A larger zirconium phosphate sorbent module can be used for multiple conditioning cycles without recharging. For example, a zirconium phosphate sorbent module containing 1,500 g of zirconium phosphate can be used for approximately 10 conditioning cycles before being replaced or recharged. Any size zirconium phosphate sorbent module can be used for conditioning the zirconium oxide sorbent modules.

Figure 5:
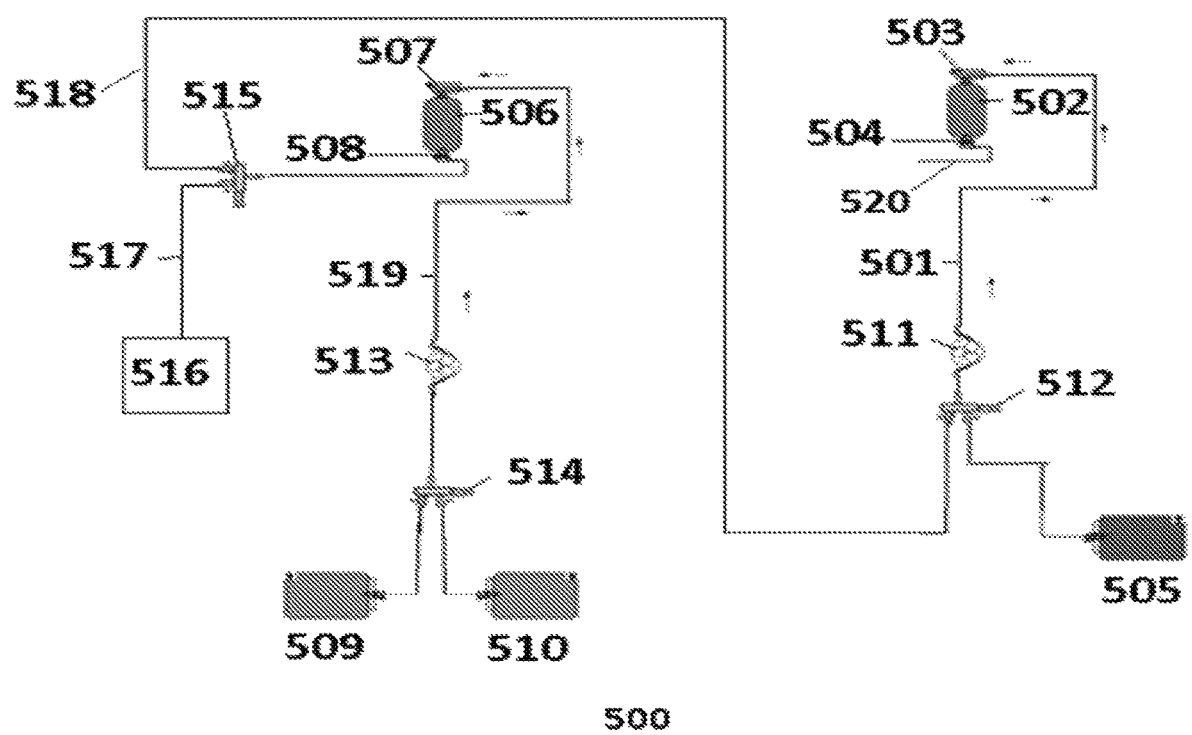
FIG. 5 shows a flow path for recharging a zirconium phosphate module, as well as recharging and conditioning a zirconium oxide module.

FIG. 5 illustrates a recharging flow path 500 for recharging both zirconium phosphate and zirconium oxide, with the recharged zirconium phosphate sorbent module 506 used to generate the conditioning solution. The zirconium oxide sorbent module 502 can be placed in a receiving compartment of the recharger and connect to a zirconium oxide recharging flow path 501 through zirconium oxide module inlet 503 and zirconium oxide module outlet 504 into effluent line 520. Pump 511 provides a driving force for moving fluid through the zirconium oxide recharging flow path 501. Base solution from base source 505 can be pumped through valve 512 and through zirconium oxide sorbent module 502 to recharge the zirconium oxide. The recharger can also have a second receiving compartment for receiving a zirconium phosphate sorbent module 506, which can connect to zirconium phosphate recharging flow path 519 through zirconium phosphate module inlet 507 and zirconium phosphate module outlet 508. The zirconium phosphate sorbent module 506 is recharged by pumping a brine solution from brine source 509 through valve 514 and zirconium phosphate sorbent module 506. The brine solution can contain acids, bases, salts, or combinations thereof. The hydrogen and sodium ions in the brine solution displace potassium, calcium, magnesium, ammonium, and other cations adsorbed by the zirconium phosphate during dialysis. Pump 513 provides a driving force for moving fluid through zirconium phosphate recharging flow path 519. The effluent exiting zirconium phosphate sorbent module outlet 508 can pass through valve 515 to drain line 517 to waste reservoir 516 or a drain (not shown). The basic effluent exiting zirconium oxide sorbent module 502 can be pumped to the same waste reservoir 516, drain (not shown) or collected separately for in a separate waste reservoir (not shown) for later disposal.

After recharging of both the zirconium oxide sorbent module 502 and zirconium phosphate sorbent module 506, the zirconium oxide sorbent module 502 can be conditioned. Bicarbonate solution from bicarbonate source 510 can be pumped through the zirconium phosphate sorbent module 506, generating a bicarbonate solution at the desired zirconium oxide effluent pH. Valve 515 can be switched to direct the bicarbonate solution into fluid connector 518 and to valve 512 in the zirconium oxide recharging flow path 501. The bicarbonate solution is pumped from valve 512 through the zirconium oxide sorbent module 502 to condition the zirconium oxide sorbent module 502.

Figure 6:
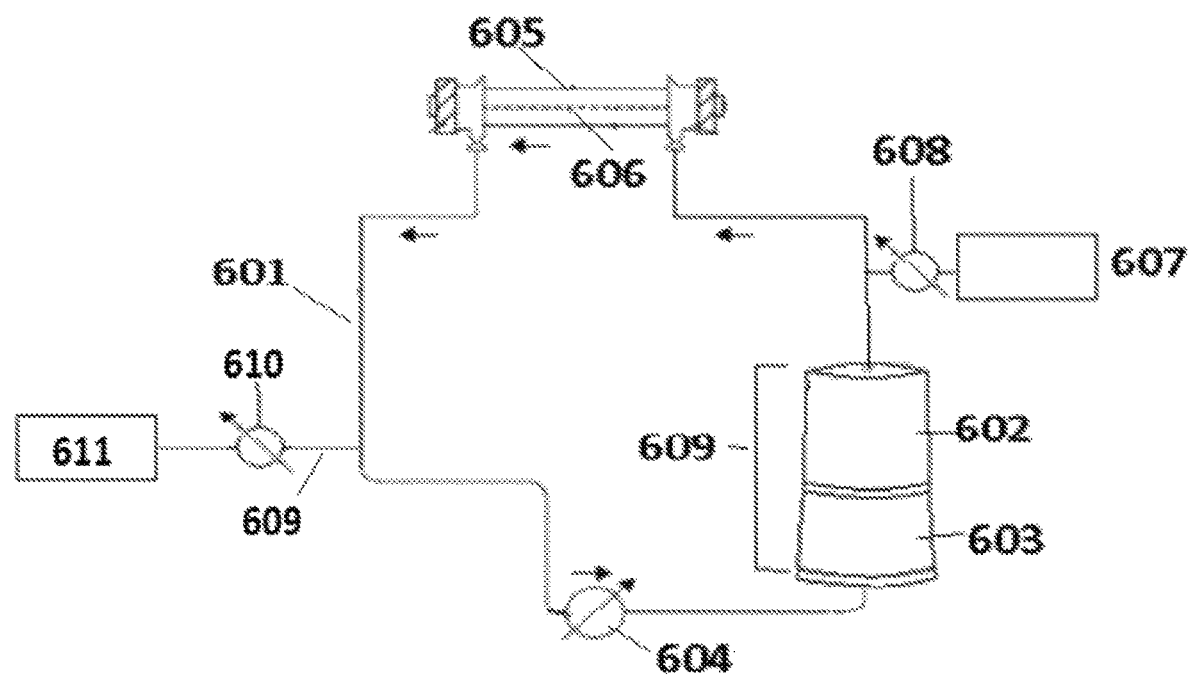
FIG. 6 shows a dialysate flow path for conditioning a zirconium oxide module during priming.

FIGS. 1-5 illustrate various methods of conditioning a recharged zirconium oxide sorbent module in either a recharger or a separate conditioning system. The recharged zirconium oxide sorbent module can also be conditioned in a dialysate flow path 601 during priming of the system, as illustrated in FIG. 6. FIG. 6 is a simplified diagram of a dialysate flow path 601. During treatment, dialysate is pumped through the dialysate flow path 601 and dialyzer 605. Pump 604 provides the driving force for pumping fluid through the dialysate flow path 601. At the same time blood is pumped through the dialyzer 605 on the opposite side of a semipermeable membrane 606. Waste products in the blood of the patient cross the semipermeable membrane 606 and enter the dialysate in the dialyzer 605. The waste products are removed from the dialysate by a sorbent cartridge 609, which includes a zirconium phosphate sorbent module 603 and a zirconium oxide sorbent module 602. One of skill in the art will understand additional materials can be included in the sorbent cartridge 609, such as activated carbon, urease, and alumina (not shown). To prime the system and the sorbent cartridge 609, a solution containing sodium bicarbonate is pumped through the dialysate flow path 601, the dialyzer 605, and the sorbent cartridge 609. In certain embodiments, the solution can also contain sodium chloride. Alternatively, the method can use a sodium bicarbonate solution followed by a sodium chloride solution, or a sodium chloride solution followed by a sodium bicarbonate solution. Water from a water source (not shown), sodium chloride from a sodium chloride source (not shown) are added to the dialysate flow path 601, and sodium bicarbonate from bicarbonate source 607 is added to the dialysate flow path 601 by pump 608. The resulting priming solution is pumped through the dialysate flow path 601 to prime the system. The priming solution, containing bicarbonate, is pumped through zirconium phosphate sorbent module 603, generating a bicarbonate solution at the desired zirconium oxide effluent pH, and then through zirconium oxide sorbent module 602, conditioning the zirconium oxide sorbent module 602. After addition of bicarbonate the priming solution can be recirculated within dialysate flow path 601 in order to maximize the utilization of bicarbonate. In certain embodiments, one pass of fluid through the dialysate flow path 601 can be conducted with adding bicarbonate, and a second pass of the fluid can be done without adding additional bicarbonate.

Conditioning the zirconium oxide sorbent module 602 during priming requires additional bicarbonate in the dialysis system and lengthens the time necessary for priming. The additional amount of bicarbonate solution needed for conditioning during priming can be about 80 to 120 g of sodium bicarbonate. Conditioning the zirconium oxide sorbent module 602 during priming also adds between 5-15 minutes to the priming process. Conditioning the zirconium oxide sorbent module 602 in a recharger or a separate conditioning system allows a smaller bicarbonate source for therapy and a faster priming process. In any embodiment, the zirconium oxide sorbent module 602 can be conditioned partly in a recharger or conditioning system, and partly during priming, reducing the additional bicarbonate necessary during priming of the system. After conditioning, excess sodium bicarbonate can be rinsed into drain line 609 by pump 610 or used in subsequent priming steps. The drain line 609 can be fluidly connected to a drain reservoir 611, or alternatively, directly to a drain (not shown).

Figure 7:
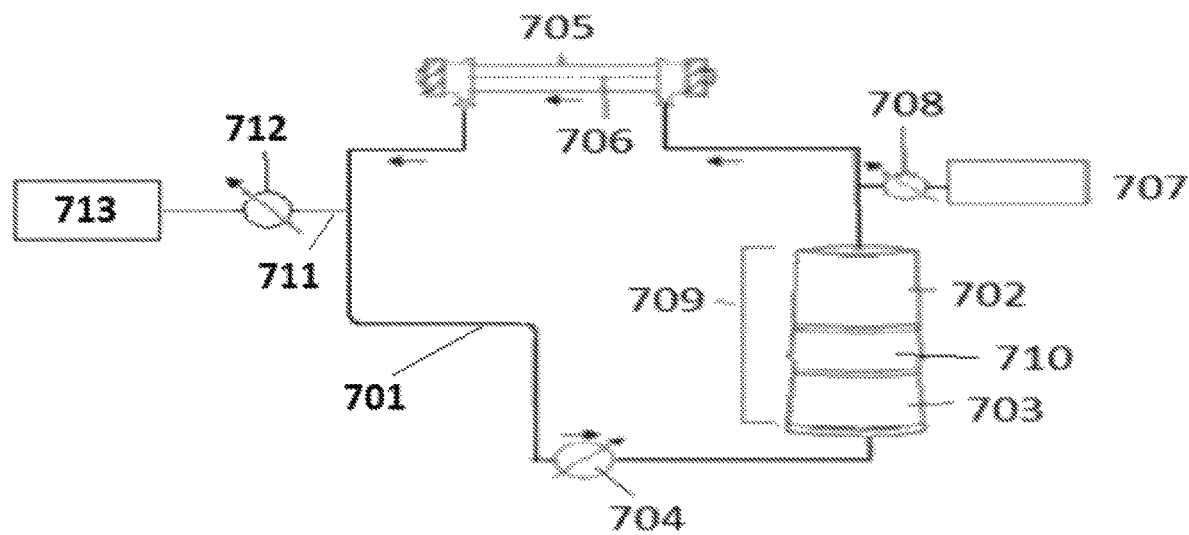
FIG. 7 shows a dialysate flow path for conditioning a zirconium oxide module with a solid bicarbonate source.

FIG. 7 is an alternative simplified diagram of a dialysate flow path 701. During treatment, dialysate is pumped through the dialysate flow path 701 and dialyzer 705. Pump 704 provides the driving force for pumping fluid through the dialysate flow path 701. At the same time blood is pumped through the dialyzer 705 on the opposite side of a semipermeable membrane 706. Waste products in the blood of the patient can cross the semipermeable membrane 706 and enter the dialysate in the dialyzer 705. The waste products are removed from the dialysate by a sorbent cartridge 709, which includes a zirconium phosphate sorbent module 710, a zirconium oxide sorbent module 702, and an additional sorbent module 703. The additional sorbent module 703 can contain a solid sodium bicarbonate or powder, which can be used to generate the conditioning solution in the dialysate flow path 701. One of skill in the art will understand that additional materials can be included in the sorbent cartridge 709, such as activated carbon, urease, and alumina (not shown). In certain embodiments, activated carbon, urease, and alumina can be contained in sorbent module 703 with the bicarbonate. Alternatively, the solid sodium bicarbonate can be placed in the same sorbent module 710 as the zirconium phosphate. To prime the system and the sorbent cartridge 709, a solution containing sodium chloride is pumped through the dialysate flow path 701, the dialyzer 705, and the sorbent cartridge 709. Water from a water source (not shown) and optionally sodium chloride from a sodium chloride source (not shown) can be added to the dialysate flow path 701. The fluid, while flowing through sorbent module 703, can dissolve the sodium bicarbonate within sorbent module 703 to generate a priming and conditioning solution containing sodium bicarbonate. In certain embodiments, the conditioning solution can also contain sodium chloride. Alternatively, the method can generate a sodium bicarbonate solution, followed by a sodium chloride solution. By using a solid sodium bicarbonate in the sorbent module 703, the size requirements for bicarbonate source 707 are reduced, and the priming and conditioning time is reduced. The resulting priming solution is pumped through the dialysate flow path 701 to prime the system. The priming solution, containing bicarbonate dissolved by fluid passing through sorbent module 703, is pumped through zirconium phosphate sorbent module 710, generating a bicarbonate solution at the desired zirconium oxide effluent pH, and then through zirconium oxide sorbent module 702, conditioning the zirconium oxide sorbent module 702.

Conditioning the zirconium oxide sorbent module 702 with a conditioning solution formed by dissolving solid sodium bicarbonate in sorbent module 703 requires a quantity of sodium bicarbonate to be initially present in the sorbent module 703. The amount of bicarbonate present in sorbent module 703 can be any amount sufficient to fully condition the zirconium oxide sorbent module 702. In certain embodiments, the amount of sodium bicarbonate placed in sorbent module 703 can be between 40 and 130 grams, between 40 and 60 grams, between 50 and 100 grams, between 50 and 130 grams, between 75 and 100 grams, or between 80 and 130 grams. The necessary amount of sodium bicarbonate can vary depending on the size of zirconium oxide sorbent module 702. In certain embodiments, an excess of sodium bicarbonate beyond that necessary for conditioning zirconium oxide sorbent module 702 can be placed in sorbent module 703. After conditioning, the excess bicarbonate can be rinsed from the dialysate flow path 701 into drain line 711 by pump 712 or used in subsequent priming steps. After generation of the bicarbonate solution the bicarbonate solution can be recirculated within dialysate flow path 701 in order to maximize the utilization of bicarbonate during priming. The drain line 711 can be fluidly connected to a drain reservoir 713, or alternatively, directly to a drain (not shown).

As described, the pH of the conditioning solution can be the same pH as the effluent from the zirconium phosphate sorbent module subsequently used in dialysis.

Figure 8:
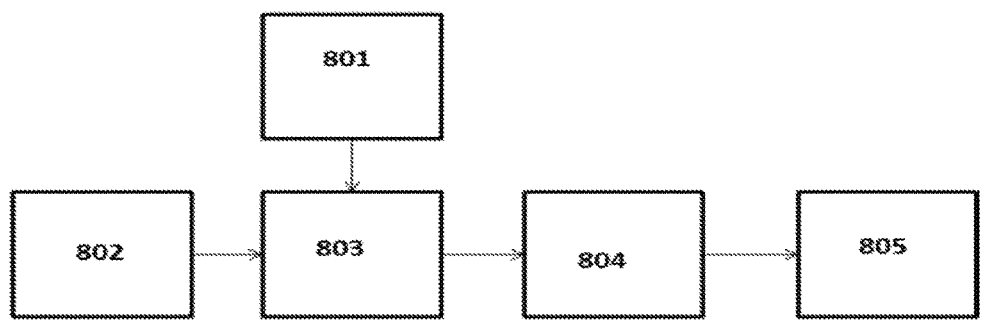
FIG. 8 is a flow chart illustrating the steps of recharging and conditioning a zirconium oxide module.

FIG. 8 is a flow chart illustrating the steps of recharging and conditioning a zirconium oxide sorbent module to the correct pH. In step 801, a desired zirconium oxide effluent pH can be determined. In step 802, the zirconium oxide sorbent module is recharged with a strong base. In step 803, the conditioning solution is generated. Any of the described methods for generating the conditioning solution can be used in step 803, including mixing a bicarbonate solution with acid, mixing a bicarbonate solution with carbon dioxide, pumping a bicarbonate solution through a dedicated or non-dedicated zirconium phosphate sorbent module either in a recharger, a conditioning system, or a dialysate flow path, or pumping water through a sorbent module containing solid sodium bicarbonate in a dialysate flow path. In step 804, the conditioning solution is pumped through the zirconium oxide sorbent module. In step 805, the zirconium oxide sorbent module is reused in dialysis.

Figure 9:
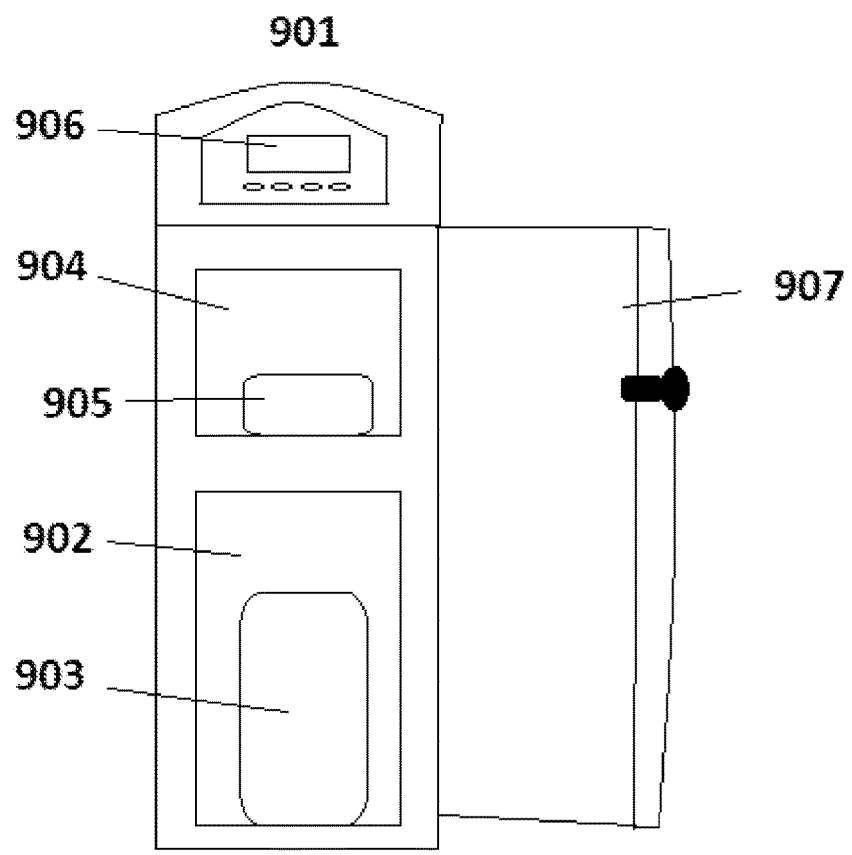
FIG. 9 shows a recharger for recharging and conditioning of zirconium oxide.

FIG. 9 illustrates a non-limiting embodiment of a recharger for recharging and conditioning zirconium oxide in a zirconium oxide module. The recharger 901 includes a zirconium oxide receiving compartment 904 for receiving a zirconium oxide sorbent module 905. The recharger 901 can also have a zirconium phosphate receiving compartment 902 for receiving a zirconium phosphate sorbent module 903. The zirconium phosphate sorbent module 903 can be a dedicated zirconium phosphate sorbent module, or a zirconium phosphate sorbent module that will be used in a subsequent dialysis session. The conditioning solution can be pumped through the zirconium phosphate sorbent module 903 and then into the zirconium oxide sorbent module 905 for conditioning. Alternatively, the conditioning solution can be generated or stored separately, and need not pass through the zirconium phosphate sorbent module 903. Door 907 controls access to the receiving compartments 902 and 904 during operation. A base source and a bicarbonate source (not shown) can be fluidly connected to the recharger 901 for recharging and conditioning of the zirconium oxide sorbent module 905. Fluid connections (not shown in FIG. 9) connect to the top and bottom of the sorbent modules 903 and 905 for passing recharging fluids into, through, and out of the reusable sorbent modules 903 and 905. A brine source (not shown) can also be provided for recharging the zirconium phosphate sorbent module 903. A user interface 906 is provided to start or control the recharging and conditioning processes by the user. The user interface 906 also provides the status of the recharging and conditioning processes to the user, such as the times of completion of each step, or a time until the processes are complete. User interface 906 also provides alert messages if any problems are detected during recharging, such as leaks, occlusions, pump failures, or mismatched chemicals. User interface 906 also allows the user to input the desired zirconium oxide effluent pH to control the conditioning process.

Although shown with receiving compartments 902 and 904 for both a zirconium oxide and zirconium phosphate sorbent module in FIG. 9, the recharger 901 can be similarly constructed with solely a zirconium oxide receiving compartment. As described, the conditioning solution can be generated separately, and need not pass through a zirconium phosphate sorbent module. The rechargers can have any number of receiving compartments for any combination of zirconium oxide and zirconium phosphate sorbent modules, including 1, 2, 3, 4, 5, 6, 7 or more receiving compartments for recharging and conditioning of any number of zirconium oxide modules.

Figure 10:
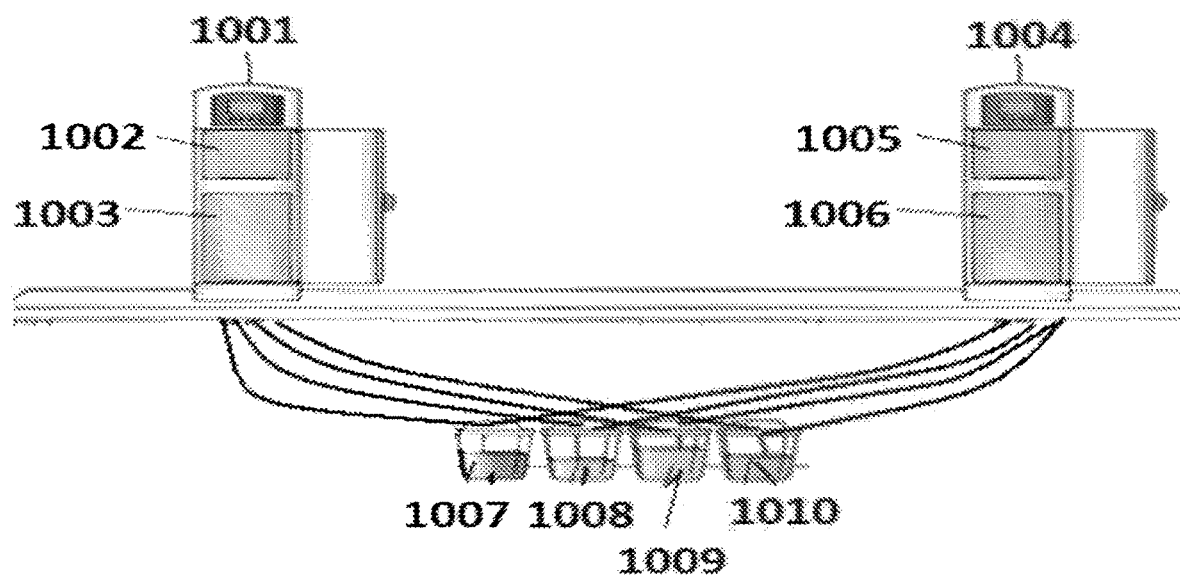
FIG. 10 shows multiple rechargers chained together for recharging and conditioning multiple zirconium oxide modules.

As illustrated in FIG. 10, multiple rechargers can be chained together and connected to a single set of fluid sources for sharing of infrastructure. A first recharger 1001 having a zirconium phosphate receiving compartment 1003 and zirconium oxide receiving compartment 1002 is fluidly connected to water source 1007, bicarbonate source 1008, disinfectant source 1009, and base source 1010. The zirconium phosphate module used can be a dedicated zirconium phosphate sorbent module, or a zirconium phosphate sorbent module that will be used in subsequent dialysis. For recharging both zirconium phosphate and zirconium oxide in the recharger, a brine source (not shown) can be included for zirconium phosphate recharging. A second recharger 1004 having a zirconium oxide receiving compartment 1005 and zirconium phosphate receiving compartment 1006 is also fluidly connected to the same water source 1007, bicarbonate source 1008, disinfectant source 1009, and base source 1010. Any number of rechargers can be connected to a common set of fluid sources, including 2, 3, 4, 5, 6 or more rechargers, each fluidly connected to a single set of fluid sources and a single set of waste reservoirs. Connecting multiple rechargers to a single set of fluid sources saves space and materials and simplifies recharging multiple sets of reusable modules in a clinic or hospital setting. Each of the rechargers may include a separate drain line and/or separate waste reservoirs, or each recharger may be fluidly connected to a common drain line. The drain line can also be fluidly connected to any one of a drain, a common reservoir, or combinations thereof. As described, the rechargers can alternatively only have zirconium oxide receiving compartments for recharging and conditioning solely of zirconium oxide.

One skilled in the art will understand that various combinations and/or modifications and variations can be made in the described systems and methods depending upon the specific needs for operation. Moreover features illustrated or described as being part of an aspect of the invention may be used in the aspect of the invention, either alone or in combination, or follow a preferred arrangement of one or more of the described elements.

We claim:

1. A method of conditioning zirconium oxide, comprising the steps of:
    pumping a conditioning solution through a zirconium oxide sorbent module in a flow path; and
    conditioning the zirconium oxide sorbent module using the conditioning solution comprising sodium bicarbonate at a desired zirconium oxide effluent pH.

2. The method of claim 1, further comprising the step of pumping a base solution through the zirconium oxide sorbent module to recharge zirconium oxide in the zirconium oxide sorbent module prior to conditioning the zirconium oxide sorbent module.

3. The method of claim 2, wherein the base solution is a sodium hydroxide solution.

4. The method of claim 1, further comprising the step of pumping the conditioning solution through a zirconium phosphate sorbent module prior to pumping the conditioning solution through the zirconium oxide sorbent module.

5. The method of claim 4, wherein the flow path is a dialysate flow path comprising the zirconium phosphate sorbent module and zirconium oxide sorbent module.

6. The method of claim 4, wherein the flow path is a recharging flow path comprising the zirconium phosphate sorbent module and zirconium oxide sorbent module.

7. The method of claim 6, wherein the recharging flow path is in a recharger.

8. The method of claim 1, wherein the desired zirconium oxide effluent pH is between 5 and 7.5.

9. The method of claim 1, further comprising the step of generating the conditioning solution in the flow path.

10. The method of claim 9, wherein the step of generating the conditioning solution comprises mixing a sodium bicarbonate solution with acid.

11. The method of claim 9, wherein the step of generating the conditioning solution comprises mixing a sodium bicarbonate solution with carbon dioxide.

12. The method of claim 1, wherein the conditioning solution is pumped through the zirconium oxide sorbent module for between 5-30 minutes.

13. The method of claim 1, further comprising the step of disinfecting the zirconium oxide sorbent module by pumping a disinfectant solution through the zirconium oxide sorbent module.

14. The method of claim 9, wherein the step of generating the conditioning solution comprises pumping a fluid in a dialysate flow path through a first sorbent module; the first sorbent module containing solid sodium bicarbonate.

15. The method of claim 10, wherein the sodium bicarbonate solution and acid are mixed in a static mixer.

16. The method of claim 13, wherein the disinfectant solution comprises at least one of bleach, peracetic acid, and/or citric acid.

17. The method of claim 11, wherein the step of mixing sodium bicarbonate solution with carbon dioxide comprises metering carbon dioxide gas into a bicarbonate source.

18. The method of claim 17, further comprising the step of monitoring a pH of the bicarbonate solution while metering the carbon dioxide gas into the bicarbonate source.

19. The method of claim 1, wherein the conditioning solution further comprises a disinfectant.

20. The method of claim 19, wherein the disinfectant is bleach.

* * * * *